(12) United States Patent
Strieter et al.

(10) Patent No.: US 9,193,775 B2
(45) Date of Patent: Nov. 24, 2015

(54) WELL-DEFINED OLIGOMERS OF UBIQUITIN AND UBIQUITIN-LIKE POLYPEPTIDES, AND METHODS FOR PREPARING SAME

(71) Applicant: Wisconsin Alumni Research Foundation, Madison, WI (US)

(72) Inventors: Eric Strieter, Madison, WI (US); Ellen Valkevich, Madison, WI (US); Robert Guenette, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 13/791,435

(22) Filed: Mar. 8, 2013

(65) Prior Publication Data

US 2013/0281659 A1  Oct. 24, 2013

Related U.S. Application Data

(60) Provisional application No. 61/624,201, filed on Apr. 13, 2012.

(51) Int. Cl.
*C07K 14/47* (2006.01)
*C07K 14/00* (2006.01)

(52) U.S. Cl.
CPC ................. *C07K 14/47* (2013.01); *C07K 14/00* (2013.01); *C07K 2319/95* (2013.01)

(58) Field of Classification Search
None
See application file for complete search history.

(56) References Cited

U.S. PATENT DOCUMENTS

2008/0064117 A1* 3/2008 Issakani et al. ............... 436/501

FOREIGN PATENT DOCUMENTS

EP     2 377 547     10/2011

OTHER PUBLICATIONS

Valkevich et al., J. Am. Chem. Soc., 2012, 134, 6916-6919.*
Jung et al., Bioconjugate Chem.,2009, 20, 1152-1162.*
Jung et al., Bioconjugate Chem., 2009, 20, 1152-1162.*
Jung et al., J. Am. Soc. Mass Spectrom., 2011, 22, 1463-1471.*
Ayaz-Guner, S., et al., "In vivo phosphorylation site mapping in mouse cardiac troponin I by high resolution top-down electron capture dissociation mass spectrometry: Ser22/23 are the only sites basally phosphorylated," Biochemistry, Sep. 2009, 48(34), pp. 8161-8170.
Ben-Saadon, R., et al., "The polycomb protein Ring1B generates self atypical mixed ubiquitin chains required for its in vitro histone H2A ligase activity," 2006, Mol. Cell, 24, pp. 701-711.
Content, et al., "Expression and preliminary deletion analysis of the 42 kDA 2-5A synthetase induced by human interferon," in Biological Interferon Systems, Proceedings of ISIR-TNO Meeting on Interferon Systems, Cantell (ed.), pp. 65-72, Nijhoff 1987.
Coumailleau et al., "Definition of a Minimal Domain of the Dioxin Receptor That Is Associated with Hsp90 and Maintains Wild Type Ligand Binding Affinity and Specificity," Journal Biological Chemistry, 1995, vol. 270, pp. 25291-25300.
Cunningham et al., "High-resolution epitope mapping of hGH-receptor interactions by alanine-scanning mutageness," Science, 1989, vol. 244, pp. 1081-1085.
de Bie, P. et al., "Regulation of the Polycomb protein RING1B ubiquitination by USP7," Biochem. Biophys. Res. Commun. Sep. 2010, 400(3), pp. 389-395.
Faesen et al., "The differential modulation of USP activity by internal regulatory domains, interactors and eight ubiquitin chain types," Chem. Biol. Dec. 2011, 18(12), pp. 1550-1561.
Fairbanks, B.D., et al., "Photoinitiated polymerization of PEG-diacrylate with lithium phenyl-2,4,6-trimethylbenzoylphosphinate: polymerization rate and cytocompatibility," Biomaterials 2009, 30, pp. 6702-6707.
Fukunaga et al. "Identification of Functional Domains of the Aryl Hydrocarbon Receptor," J. Biol. Chem., 1995, vol. 270, pp. 29270-29278.
Ge et al., "Top-down high-resolution mass spectrometry of cardiac myosin binding protein C revealed that truncation alters protein phosphorylation state ," Proc. Natl. Acad. Sci., 2009, vol. 106, pp. 12658-12663.
Herschman, The EGF Receptor, in Control of Animal Cell Proliferation 1, Boynton et al, (eds), Academic Press, 1985, pp. 169-199.
Ho, et al., "Site-directed mutagenesis by overlap extension using the polymerase chain reaction," Gene 1989, 77, 51-59.
Jockusch, S., et al., "Phosphinoyl Radicals: Structure and Reactivity. A Laser Flash Photolysis and Time-Resolved ESR Investigation," J. Am. Chem. Soc. 1998, 120, pp. 11773-11777.
Majima, T. et al., "Phenyl-2,4,6-trimethylbenzoylphosphinates as water-soluble photoinitiators. Generation and reactivity of OP(C6H5)(O—) radical anions," Makromol. Chem. 1991, 192, pp. 2307-2315.
Meisel et al., "The Conserved ELK-Homeodomain of KNOTTED-1 Contains Two Nuclear Localization Signal Sequences," 1996, Plant Molec. Biol., 30, pp. 1-14.
Pickart, C.M., et al., "Controlled synthesis of polyubiquitin chains," Meth. Enzymol. 2005, 399, 21-36.
Treuter et al., "Promoter specificity and deletion analysis of three heat stress transcription factors of tomato," Mol. Gen Genet., Jul. 1993, vol. 1, pp. 113-125.

(Continued)

*Primary Examiner* — Karlheinz R Skowronek
*Assistant Examiner* — Roy Teller
(74) *Attorney, Agent, or Firm* — Foley & Lardner LLP

(57) ABSTRACT

The present technology relates to well-defined oligomers comprising two or more monomers wherein each monomer is independently selected from a ubiquitin polypeptide or a ubiquitin-like polypeptide, and the monomers are covalently linked to each other via a thioether group or groups. Further provided are monomer building blocks and methods of making the monomers and oligomers.

24 Claims, 23 Drawing Sheets

(56) References Cited

OTHER PUBLICATIONS

Valkevich E., et al., "Forging Isopeptide Bonds Using Thiol-Ene Chemistry: Site-Specific Coupling of Ubiquitin Molecules for Studying the Activity of Isopeptidases," Journal of the American Chemical Society, 2012, vol. 134, No. 16, pp. 6916-6919.

Yamaguchi et al., "Functional analysis of aryl hydrocarbon receptor nuclear translocator interactions with aryl hydrocarbon receptor in the yeast two-hybrid system," Oct. 1995, Biochem. Pharmacol., 50(8), pp. 1295-1302.

Zhang et al., "Top-Down quantitative proteomics identified phosphorylation of cardiac troponin I as a candidate biomarker for chronic heart failure," J. Proteome Res. 2011, 10, pp. 4054-4065.

* cited by examiner

```
                         SEQUENCE LISTING

<160> NUMBER OF SEQ ID NOS: 96

<210> SEQ ID NO 1
   <211> LENGTH: 76
   <212> TYPE: PRT
   <213> ORGANISM: Homo sapiens

<400> SEQUENCE: 1

Met Gln Ile Phe Val Lys Thr Leu Thr Gly Lys Thr Ile Thr Leu Glu
   1               5                   10                  15

Val Glu Pro Ser Asp Thr Ile Glu Asn Val Lys Ala Lys Ile Gln Asp
                   20                  25                  30

Lys Glu Gly Ile Pro Pro Asp Gln Gln Arg Leu Ile Phe Ala Gly Lys
               35                  40                  45

Gln Leu Glu Asp Gly Arg Thr Leu Ser Asp Tyr Asn Ile Gln Lys Glu
       50                  55                  60

Ser Thr Leu His Leu Val Leu Arg Leu Arg Gly Gly
   65                  70                  75

<210> SEQ ID NO 2
   <211> LENGTH: 101
   <212> TYPE: PRT
   <213> ORGANISM: Homo sapiens

<400> SEQUENCE: 2

Met Ser Asp Gln Glu Ala Lys Pro Ser Thr Glu Asp Leu Gly Asp Lys
   1               5                   10                  15

Lys Glu Gly Glu Tyr Ile Lys Leu Lys Val Ile Gly Gln Asp Ser Ser
                   20                  25                  30

Glu Ile His Phe Lys Val Lys Met Thr Thr His Leu Lys Lys Leu Lys
               35                  40                  45

Glu Ser Tyr Cys Gln Arg Gln Gly Val Pro Met Asn Ser Leu Arg Phe
       50                  55                  60

Leu Phe Glu Gly Gln Arg Ile Ala Asp Asn His Thr Pro Lys Glu Leu
   65                  70                  75                  80

Gly Met Glu Glu Glu Asp Val Ile Glu Val Tyr Gln Glu Gln Thr Gly
                   85                  90                  95

Gly His Ser Thr Val
                   100

<210> SEQ ID NO 3
   <211> LENGTH: 95
   <212> TYPE: PRT
   <213> ORGANISM: Homo sapiens

<400> SEQUENCE: 3

Met Ala Asp Glu Lys Pro Lys Glu Gly Val Lys Thr Glu Asn Asn Asp
   1               5                   10                  15

His Ile Asn Leu Lys Val Ala Gly Gln Asp Gly Ser Val Val Gln Phe
                   20                  25                  30
```

-continued

Lys Ile Lys Arg His Thr Pro Leu Ser Lys Leu Met Lys Ala Tyr Cys
            35                  40                  45

Glu Arg Gln Gly Leu Ser Met Arg Gln Ile Arg Phe Arg Phe Asp Gly
        50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 4
<211> LENGTH: 103
<212> TYPE: PRT
<213> ORGANISM: Homo sapiens

<400> SEQUENCE: 4

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
                20                  25                  30

Ile Lys Arg His Thr Pro Leu Ser Lys Leu Met Lys Ala Tyr Cys Glu
            35                  40                  45

Arg Gln Gly Leu Ser Met Arg Gln Ile Arg Phe Arg Phe Asp Gly Gln
        50                  55                  60

Pro Ile Asn Glu Thr Asp Thr Pro Ala Gln Leu Glu Met Glu Asp Glu
65                  70                  75                  80

Asp Thr Ile Asp Val Phe Gln Gln Gln Thr Gly Gly Val Pro Glu Ser
                85                  90                  95

Ser Leu Ala Gly His Ser Phe
            100

<210> SEQ ID NO 5
<211> LENGTH: 165
<212> TYPE: PRT
<213> ORGANISM: Homo sapiens

<400> SEQUENCE: 5

Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
                20                  25                  30

Thr Gln Lys Ile Gly Val His Ala Phe Gln Gln Arg Leu Ala Val His
            35                  40                  45

Pro Ser Gly Val Ala Leu Gln Asp Arg Val Pro Leu Ala Ser Gln Gly
        50                  55                  60

Leu Gly Pro Gly Ser Thr Val Leu Leu Val Val Asp Lys Cys Asp Glu
65                  70                  75                  80

Pro Leu Asn Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
        115                 120                 125

Lys Pro Leu Glu Asp Gln Leu Pro Leu Gly Glu Tyr Gly Leu Lys Pro
    130                 135                 140

Leu Ser Thr Val Phe Met Asn Leu Arg Leu Arg Gly Gly Gly Thr Glu
145                 150                 155                 160

Pro Gly Gly Arg Ser
                165

<210> SEQ ID NO 6
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 7
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 8
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

```
Ser Thr Leu His Leu Val Leu Arg Leu Arg Gly Gly
 65                  70                  75
```

<210> SEQ ID NO 9
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Cys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly
 65                  70                  75
```

<210> SEQ ID NO 10
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Cys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly
 65                  70                  75
```

<210> SEQ ID NO 11
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Cys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly
```

65              70              75

<210> SEQ ID NO 12
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 13
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gln Ile Phe Val Cys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 14
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gln Ile Phe Val Cys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

```
<210> SEQ ID NO 15
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 16
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 17
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 18
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 19
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gln Ile Phe Val Lys Thr Leu Thr Gly Cys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 20
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

```
<210> SEQ ID NO 21
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 22
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 23
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 24
```

<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 25
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 26
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 27
<211> LENGTH: 76

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 28
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 29
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 30
<211> LENGTH: 76
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 30

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 31
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 32
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 33
<211> LENGTH: 76
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 33

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 34
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gln Ile Phe Val Cys Thr Leu Thr Gly Cys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 35
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Gln Ile Phe Val Cys Thr Leu Thr Gly Cys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 36
<211> LENGTH: 76
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 36

Met Gln Ile Phe Val Cys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 37
<211> LENGTH: 76
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 37

Met Gln Ile Phe Val Cys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 38
<211> LENGTH: 76
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

Met Gln Ile Phe Val Cys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 39
<211> LENGTH: 76
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Met Gln Ile Phe Val Cys Thr Leu Thr Gly Lys Thr Ile Thr Leu Glu
1               5                   10                  15

Val Glu Pro Ser Asp Thr Ile Glu Asn Val Cys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 40
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gln Ile Phe Val Cys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 41
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gln Ile Phe Val Cys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 42
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gln Ile Phe Val Cys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 43
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 44
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 45
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 46
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 47
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 48
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Cys
            35                  40                  45

Gln Leu Glu Asp Gly Arg Thr Leu Ser Asp Tyr Asn Ile Gln Cys Glu
        50                  55                  60

Ser Thr Leu His Leu Val Leu Arg Leu Arg Gly Gly
65                  70                  75

<210> SEQ ID NO 49
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gln Ile Phe Val Lys Thr Leu Thr Gly Cys Thr Ile Thr Leu Glu
1               5                   10                  15

Val Glu Pro Ser Asp Thr Ile Glu Asn Val Cys Ala Cys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75

<210> SEQ ID NO 50
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gln Ile Phe Val Lys Thr Leu Thr Gly Cys Thr Ile Thr Leu Glu
1               5                   10                  15

Val Glu Pro Ser Asp Thr Ile Glu Asn Val Cys Ala Lys Ile Gln Asp
                20                  25                  30

Cys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75

<210> SEQ ID NO 51
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Gln Ile Phe Val Lys Thr Leu Thr Gly Cys Thr Ile Thr Leu Glu
1               5                   10                  15

Val Glu Pro Ser Asp Thr Ile Glu Asn Val Cys Ala Lys Ile Gln Asp
                20                  25                  30

Lys Glu Gly Ile Pro Pro Asp Gln Gln Arg Leu Ile Phe Ala Gly Cys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75

<210> SEQ ID NO 52
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gln Ile Phe Val Lys Thr Leu Thr Gly Cys Thr Ile Thr Leu Glu
1               5                   10                  15

Val Glu Pro Ser Asp Thr Ile Glu Asn Val Cys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Cys Glu
        50                  55                  60

Ser Thr Leu His Leu Val Leu Arg Leu Arg Gly Gly
65                  70                  75

<210> SEQ ID NO 53
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Cys Ile Gln Asp
                20                  25                  30

Cys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75

<210> SEQ ID NO 54
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gln Ile Phe Val Lys Thr Leu Thr Gly Cys Thr Ile Thr Leu Glu

```
1               5                   10                  15
Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 55
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75
```

<210> SEQ ID NO 56
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 57
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Gln Ile Phe Val Lys Thr Leu Thr Gly Lys Thr Ile Thr Leu Glu
1               5                   10                  15
```

```
Val Glu Pro Ser Asp Thr Ile Glu Asn Val Lys Ala Lys Ile Gln Asp
            20                  25                  30

Cys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 58
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
            35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 59
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Cys Ile Gln Asp
            20                  25                  30

Cys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 60
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gln Ile Phe Val Lys Thr Leu Thr Gly Lys Thr Ile Thr Leu Glu
1               5                   10                  15
```

Val Glu Pro Ser Asp Thr Ile Glu Asn Val Cys Ala Cys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 61
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Cys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg Gly Gly
65                  70                  75

<210> SEQ ID NO 62
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
            20                  25                  30

Cys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 63
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp

```
                    20                  25                  30

Cys Glu Gly Ile Pro Pro Asp Gln Gln Arg Leu Ile Phe Ala Gly Lys
                35                  40                  45

Gln Leu Glu Asp Gly Arg Thr Leu Ser Asp Tyr Asn Ile Gln Cys Glu
        50                  55                  60

Ser Thr Leu His Leu Val Leu Arg Leu Arg Gly Gly
65                  70                  75

<210> SEQ ID NO 64
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gln Ile Phe Val Lys Thr Leu Thr Gly Lys Thr Ile Thr Leu Glu
1               5                   10                  15

Val Glu Pro Ser Asp Thr Ile Glu Asn Val Cys Ala Lys Ile Gln Asp
                20                  25                  30

Lys Glu Gly Ile Pro Pro Asp Gln Gln Arg Leu Ile Phe Ala Gly Cys
                35                  40                  45

Gln Leu Glu Asp Gly Arg Thr Leu Ser Asp Tyr Asn Ile Gln Cys Glu
        50                  55                  60

Ser Thr Leu His Leu Val Leu Arg Leu Arg Gly Gly
65                  70                  75

<210> SEQ ID NO 65
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Cys Ile Gln Asp
                20                  25                  30

Cys Glu Gly Ile Pro Pro Asp Gln Gln Arg Leu Ile Phe Ala Gly Cys
                35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75

<210> SEQ ID NO 66
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Cys Ile Gln Asp
                20                  25                  30
```

-continued

```
Cys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Cys Glu
 50                  55                  60

Ser Thr Leu His Leu Val Leu Arg Leu Arg Gly Gly
 65                  70                  75

<210> SEQ ID NO 67
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Cys Ile Gln Asp
                 20                  25                  30

Lys Glu Gly Ile Pro Pro Asp Gln Gln Arg Leu Ile Phe Ala Gly Cys
         35                  40                  45

Gln Leu Glu Asp Gly Arg Thr Leu Ser Asp Tyr Asn Ile Gln Cys Glu
 50                  55                  60

Ser Thr Leu His Leu Val Leu Arg Leu Arg Gly Gly
 65                  70                  75

<210> SEQ ID NO 68
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                 20                  25                  30

Cys Glu Gly Ile Pro Pro Asp Gln Gln Arg Leu Ile Phe Ala Gly Cys
         35                  40                  45

Gln Leu Glu Asp Gly Arg Thr Leu Ser Asp Tyr Asn Ile Gln Cys Glu
 50                  55                  60

Ser Thr Leu His Leu Val Leu Arg Leu Arg Gly Gly
 65                  70                  75

<210> SEQ ID NO 69
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Ala Asp Glu Lys Pro Lys Glu Gly Val Cys Thr Glu Asn Asn Asp
 1               5                  10                  15

His Ile Asn Leu Lys Val Ala Gly Gln Asp Gly Ser Val Val Gln Phe
                 20                  25                  30
```

```
Lys Ile Lys Arg His Thr Pro Leu Ser Lys Leu Met Lys Ala Tyr Cys
         35                  40                  45

Glu Arg Gln Gly Leu Ser Met Arg Gln Ile Arg Phe Arg Phe Asp Gly
 50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95

<210> SEQ ID NO 70
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Ala Asp Glu Lys Pro Lys Glu Gly Val Lys Thr Glu Asn Asn Asp
 1               5                  10                  15

His Ile Asn Leu Cys Val Ala Gly Gln Asp Gly Ser Val Val Gln Phe
             20                  25                  30

Lys Ile Lys Arg His Thr Pro Leu Ser Lys Leu Met Lys Ala Tyr Cys
         35                  40                  45

Glu Arg Gln Gly Leu Ser Met Arg Gln Ile Arg Phe Arg Phe Asp Gly
 50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95

<210> SEQ ID NO 71
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Ala Asp Glu Lys Pro Lys Glu Gly Val Lys Thr Glu Asn Asn Asp
 1               5                  10                  15

His Ile Asn Leu Lys Val Ala Gly Gln Asp Gly Ser Val Val Gln Phe
             20                  25                  30

Cys Ile Lys Arg His Thr Pro Leu Ser Lys Leu Met Lys Ala Tyr Cys
         35                  40                  45

Glu Arg Gln Gly Leu Ser Met Arg Gln Ile Arg Phe Arg Phe Asp Gly
 50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95

<210> SEQ ID NO 72
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 72

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Cys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 73
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Cys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 74
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ala Asp Glu Lys Pro Lys Glu Gly Val Cys Thr Glu Asn Asn Asp
1               5                   10                  15

His Ile Asn Leu Cys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

```
<210> SEQ ID NO 75
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ala Asp Glu Lys Pro Lys Glu Gly Val Cys Thr Glu Asn Asn Asp
1               5                   10                  15

His Ile Asn Leu Lys Val Ala Gly Gln Asp Gly Ser Val Val Gln Phe
            20                  25                  30

Cys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 76
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ala Asp Glu Lys Pro Lys Glu Gly Val Cys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Cys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 77
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Ala Asp Glu Lys Pro Lys Glu Gly Val Cys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Cys Ala Tyr Cys
        35                  40                  45

Glu Arg Gln Gly Leu Ser Met Arg Gln Ile Arg Phe Arg Phe Asp Gly
    50                  55                  60
```

```
Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95
```

<210> SEQ ID NO 78
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Ala Asp Glu Lys Pro Lys Glu Gly Val Lys Thr Glu Asn Asn Asp
  1               5                  10                  15

His Ile Asn Leu Cys Val Ala Gly Gln Asp Gly Ser Val Val Gln Phe
                 20                  25                  30

Cys Ile Lys Arg His Thr Pro Leu Ser Lys Leu Met Lys Ala Tyr Cys
             35                  40                  45

Glu Arg Gln Gly Leu Ser Met Arg Gln Ile Arg Phe Arg Phe Asp Gly
         50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95
```

<210> SEQ ID NO 79
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Met Ala Asp Glu Lys Pro Lys Glu Gly Val Lys Thr Glu Asn Asn Asp
  1               5                  10                  15

His Ile Asn Leu Cys Val Ala Gly Gln Asp Gly Ser Val Val Gln Phe
                 20                  25                  30

Lys Ile Lys Arg His Thr Pro Leu Ser Cys Leu Met Lys Ala Tyr Cys
             35                  40                  45

Glu Arg Gln Gly Leu Ser Met Arg Gln Ile Arg Phe Arg Phe Asp Gly
         50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95
```

<210> SEQ ID NO 80
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Met Ala Asp Glu Lys Pro Lys Glu Gly Val Lys Thr Glu Asn Asn Asp
  1               5                  10                  15
```

His Ile Asn Leu Cys Val Ala Gly Gln Asp Gly Ser Val Val Gln Phe
              20                  25                  30

Lys Ile Lys Arg His Thr Pro Leu Ser Lys Leu Met Cys Ala Tyr Cys
         35                  40                  45

Glu Arg Gln Gly Leu Ser Met Arg Gln Ile Arg Phe Arg Phe Asp Gly
     50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                 85                  90                  95

<210> SEQ ID NO 81
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
              20                  25                  30

Cys Ile Lys Arg His Thr Pro Leu Ser Cys Leu Met Lys Ala Tyr Cys
         35                  40                  45

Glu Arg Gln Gly Leu Ser Met Arg Gln Ile Arg Phe Arg Phe Asp Gly
     50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                 85                  90                  95

<210> SEQ ID NO 82
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
              20                  25                  30

Cys Ile Lys Arg His Thr Pro Leu Ser Lys Leu Met Cys Ala Tyr Cys
         35                  40                  45

Glu Arg Gln Gly Leu Ser Met Arg Gln Ile Arg Phe Arg Phe Asp Gly
     50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                 85                  90                  95

<210> SEQ ID NO 83
<211> LENGTH: 95
<212> TYPE: PRT
<213> ORGANISM: Artificial Sequence
<220> FEATURE:

-continued

<223> OTHER INFORMATION: Description of Artificial Sequence: Synthetic
polypeptide

<400> SEQUENCE: 83

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Cys Leu Met Cys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggcggtcata tgcagatctt cgtcaag                                       27

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggcggtgcgg ccgctcaacc acctcttagt ct                                 32

<210> SEQ ID NO 86
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 86

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg
65                  70

```
<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Ser Asp Tyr Asn Ile Gln Cys Glu Ser Thr Leu His
1               5                   10

<210> SEQ ID NO 88
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 88

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Gln Ile Phe Val Cys Thr Leu Thr Gly Lys Thr
1               5                   10

<210> SEQ ID NO 90
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 90

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45
```

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 91
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 91

Met Gln Ile Phe Val Cys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Ile Phe Ala Gly Cys Gln Leu Glu Asp Gly
1               5                   10

<210> SEQ ID NO 93
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 93

Met Gln Ile Phe Val Lys Thr Leu Thr Gly Cys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

```
<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Thr Leu Thr Gly Cys Thr Ile Thr Leu Glu
1               5                   10

<210> SEQ ID NO 95
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 95

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Cys
        35                  40                  45

Gln Leu Glu Asp Gly Arg Thr Leu Ser Asp Tyr Asn Ile Gln Cys Glu
    50                  55                  60

Ser Thr Leu His Leu Val Leu Arg Leu Arg
65                  70

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Tyr Asn Ile Gln Cys Glu Ser Thr Leu His Leu
1               5                   10
```

WELL-DEFINED OLIGOMERS OF UBIQUITIN AND UBIQUITIN-LIKE POLYPEPTIDES, AND METHODS FOR PREPARING SAME

CROSS-REFERENCE TO RELATED APPLICATIONS

This application claims priority to U.S. Provisional Patent Application No. 61/624,201 filed Apr. 13, 2012, the entire disclosure of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jun. 21, 2013, is named 032026-1264 SL.txt and is 77,117 bytes in size.

BACKGROUND

Covalent attachment of ubiquitin (Ub) and ubiquitin-like proteins (Ubls) to the ε-amino group of lysine residues in a target protein (including ubiquitin itself), a process termed ubiquitination, is one of the most prevalent mechanisms for regulating protein function and stability in eukaryotes. Indeed, sequence annotations suggest nearly 5% of the human genome is dedicated to the coupling and removal of Ub/Ubls to and from proteins. Given the central role of the ub network in cellular physiology, misregulation is often associated with numerous human diseases including. e.g., cancer, immune disorders neurodegenerative diseases and congestive heart failure.

Ubiquitination is unique among the ensemble of posttranslational modifications (PTMs), specifically from the standpoint of signal diversity. For example, in contrast to other prevalent PTMs such as phosphorylation, proteins can be modified with Ub on a single lysine residue (monoUb), multiple lysines (multi-monoUb), or a single lysine with a polymeric chain of Ub (polyUb). With regards to polyUb chain formation, Ub possesses seven lysine residues (K6, K11, K27, K29, K33, K48, and K63), each of which may form an isopeptide linkage with the carboxy terminus of another Ub molecule. This feature adds significant complexity to intracellular Ub signaling networks as it permits the assembly of chains with many different types of linkages and lengths with the potential to control distinct biological processes.

A number of reports have recently emerged describing chemical approaches to the site-specific conjugation of Ub molecules through native Nε-Gly-L-Lys isopeptide linkages as well as various normative linkages. Indeed, some of the methods have elucidated important structural distinctions for Ub dimers linked through the different Ub lysines, and enabled studies that uncovered how the structure and function of target proteins is altered upon Ub modification. However, many of the chemical approaches designed to recapitulate the Nε-Gly-L-Lys linkage suffer from drawbacks such as instability, lengthy synthetic manipulations, and/or the use of specialized recombinant DNA technologies for incorporating unnatural amino acids. Moreover, branched Ub oligomers in which two or more Ub molecules are covalently attached to a single Ub through different lysines appear to be inaccessible using known methods.

SUMMARY

The present technology provides well-defined oligomers of Ub and Ubl polypeptides constructed using thioether groups rather than the naturally occurring isopeptide linkages. The thioether groups can be designed to closely mimic the native isopeptide or may be varied. Also provided are the Ub and Ubl building blocks, i.e., monomers, for constructing the oligomers, including Ub and Ubl polypeptides with carboxy terminal alkenes. Methods of preparing the monomers are also disclosed. The present technology further includes methods of coupling the monomers to efficiently and precisely form the Ub and Ubl oligomers. Oligomers of the present technology may be used to probe the roles of the analogous natural Ub and Ubl oligomers in cellular physiology and human disease.

(B) Map of observed fragments. Data analysis for the map on top (core peptide disclosed as SEQ ID NO: 86) includes Nϵ-Gly-L-homothiaLys thioether linker modification at cysteine-63 (red) in c and z* ion predictions. Bottom map (SEQ ID NO: 86) does not include thioether linker modification in theoretical analysis. (C) Key ECD fragment ions for mapping thioether linkage site on UbK63C (SEQ ID NOS 87 and 87). Circles represent theoretical isotopic abundance distribution of the isotopomer peaks. Calc'd: calculated most abundant molecular weight. Expt'l: experimental most abundant molecular weight.

Figure 9:
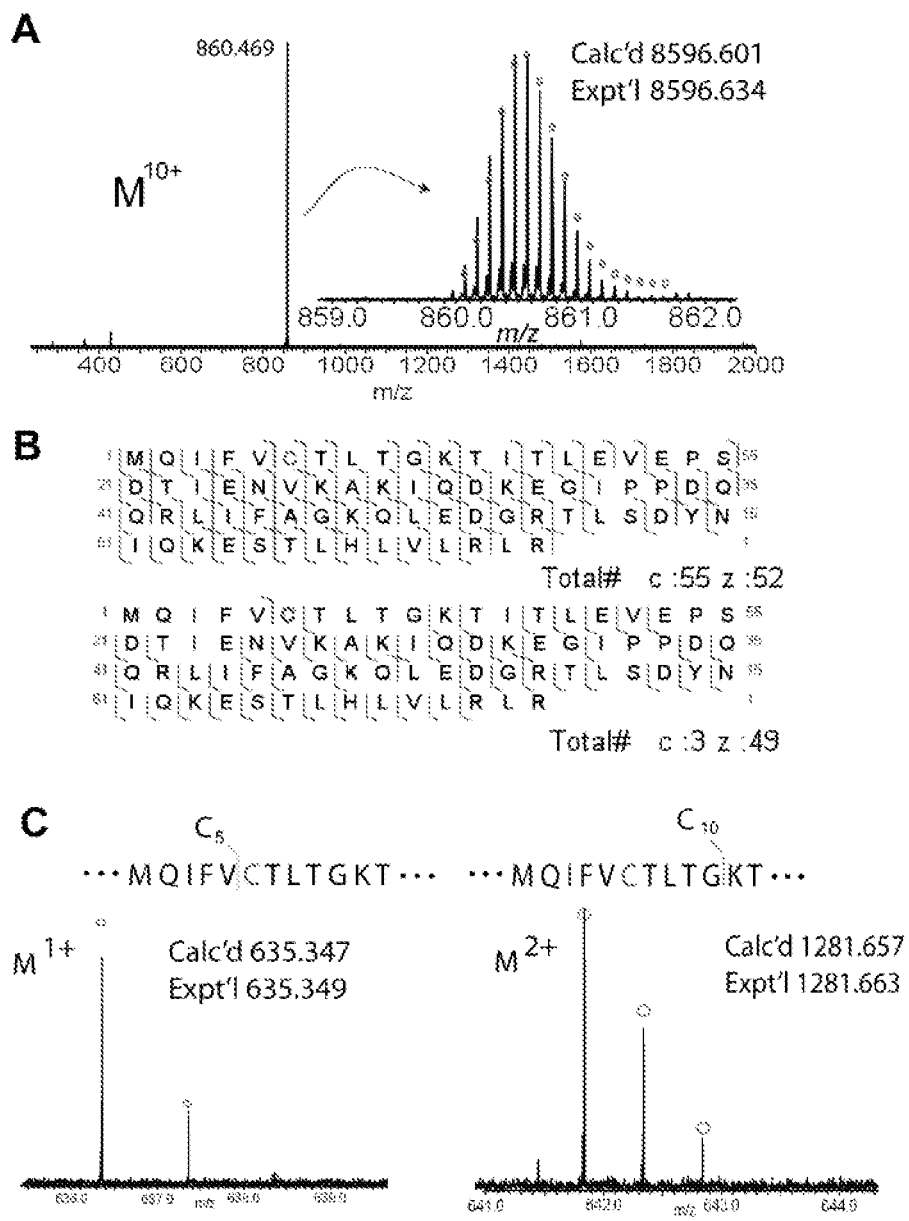

FIG. 9. ECD analysis of K6C-linked dimer, according to the Examples: (A) K6C-linked $Ub_{1-74}$ GlyGly-AA parent ion isolation ($M^{10+}$ charge state) with insert of isotopomers. (B) Map of observed fragments. Data analysis for the map on top (core peptide disclosed as SEQ ID NO: 88) includes Nϵ-Gly-L-homothiaLys thioether linker modification at cysteine-6 (red) in c and z* ion predictions. Bottom map (SEQ ID NO: 88) does not include thioether linker modification in theoretical analysis. (C) Key ECD fragment ions for mapping thioether linkage site on UbK6C (SEQ ID NOS 89 and 89). Circles represent theoretical isotopic abundance distribution of the isotopomer peaks. Calc'd: calculated most abundant mass. Expt'l: experimental most abundant mass.

Figure 10:
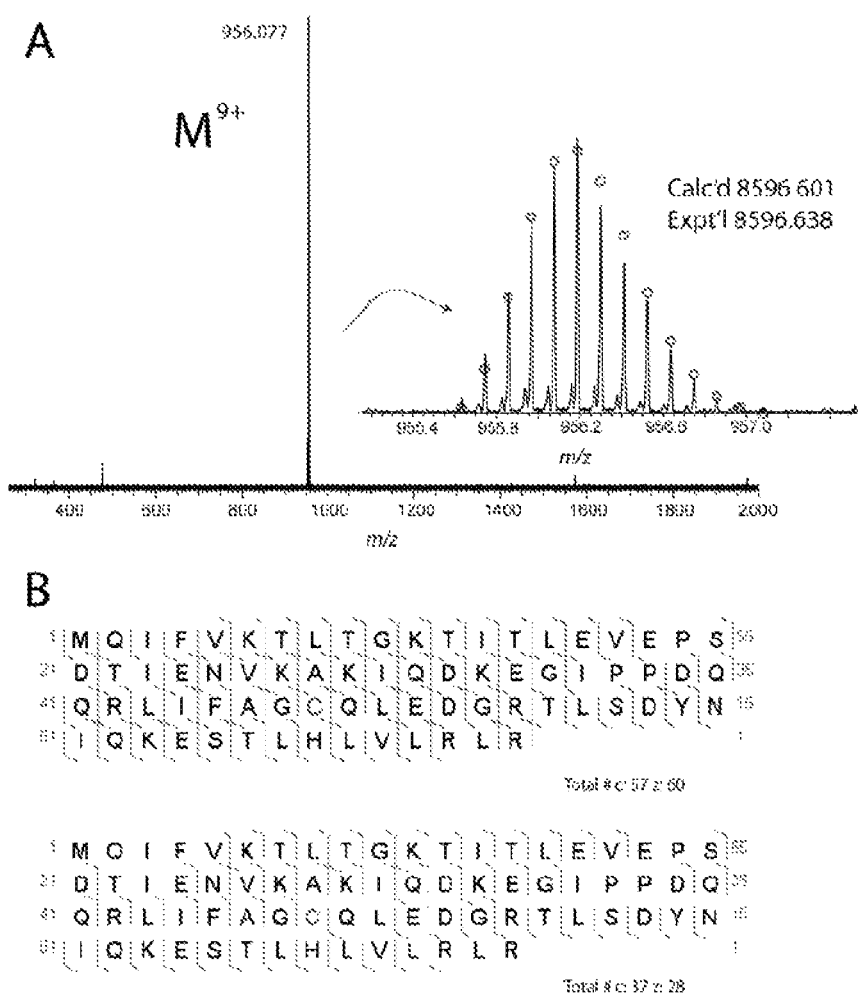

FIG. 10. ECD analysis of K48C-linked Ub dimer, according to the Examples: (A) K48C-linked $Ub_{1-74}$ GlyGly-AA parent ion isolation ($M^{9+}$ charge state) with insert of isotopomers. (B) Map of observed fragments. Data analysis for the map on top (core peptide disclosed as SEQ ID NO: 90) includes Nϵ-Gly-L-homothiaLys thioether linker modification at cysteine-48 (red) in c and z* ion predictions. Bottom map (SEQ ID NO: 90) does not include thioether linker modification in theoretical analysis.

Figure 11:
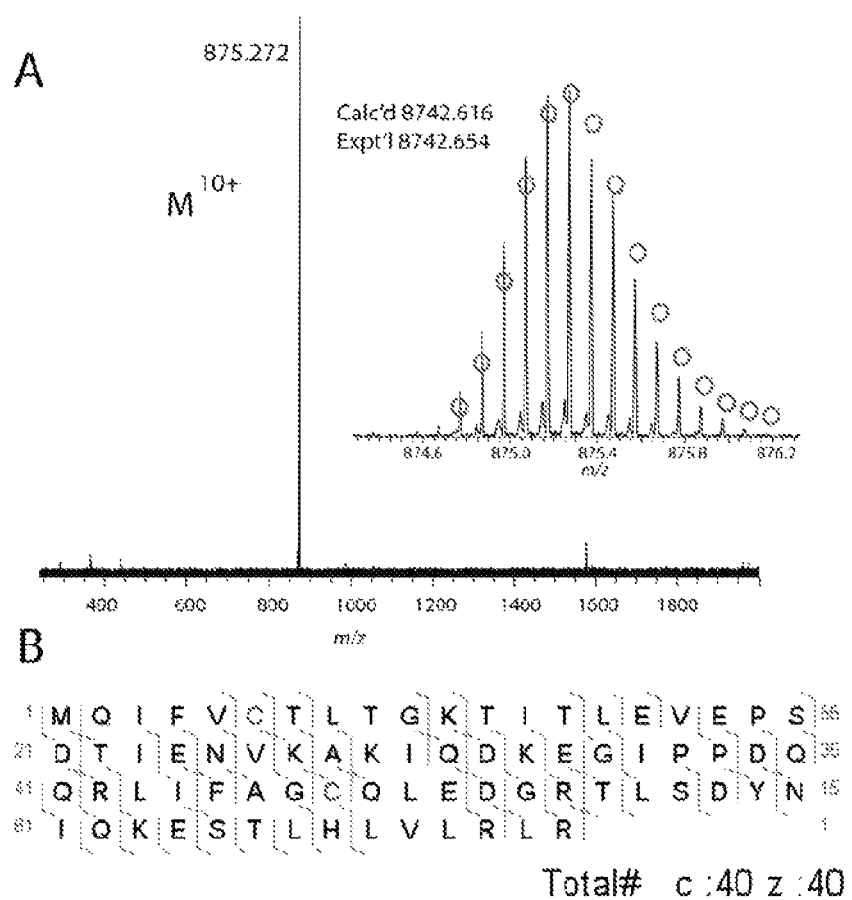

FIG. 11. ECD analysis of K6C, K48C-linked branched Ub trimer, according to the Examples: (A) K6C, K48C $Ub_{1-74}$ GlyGlyAA$_2$ parent ion isolation ($M^{10+}$ charge state) with insert of isotopomers. (B) Map of observed fragments (core peptide disclosed as SEQ ID NO: 91). Data analysis includes Nϵ-Gly-L-homothiaLys thioether linker modification at cysteine-6 and cysteine-48 (red) in c and z* ion predictions.

Figure 12:
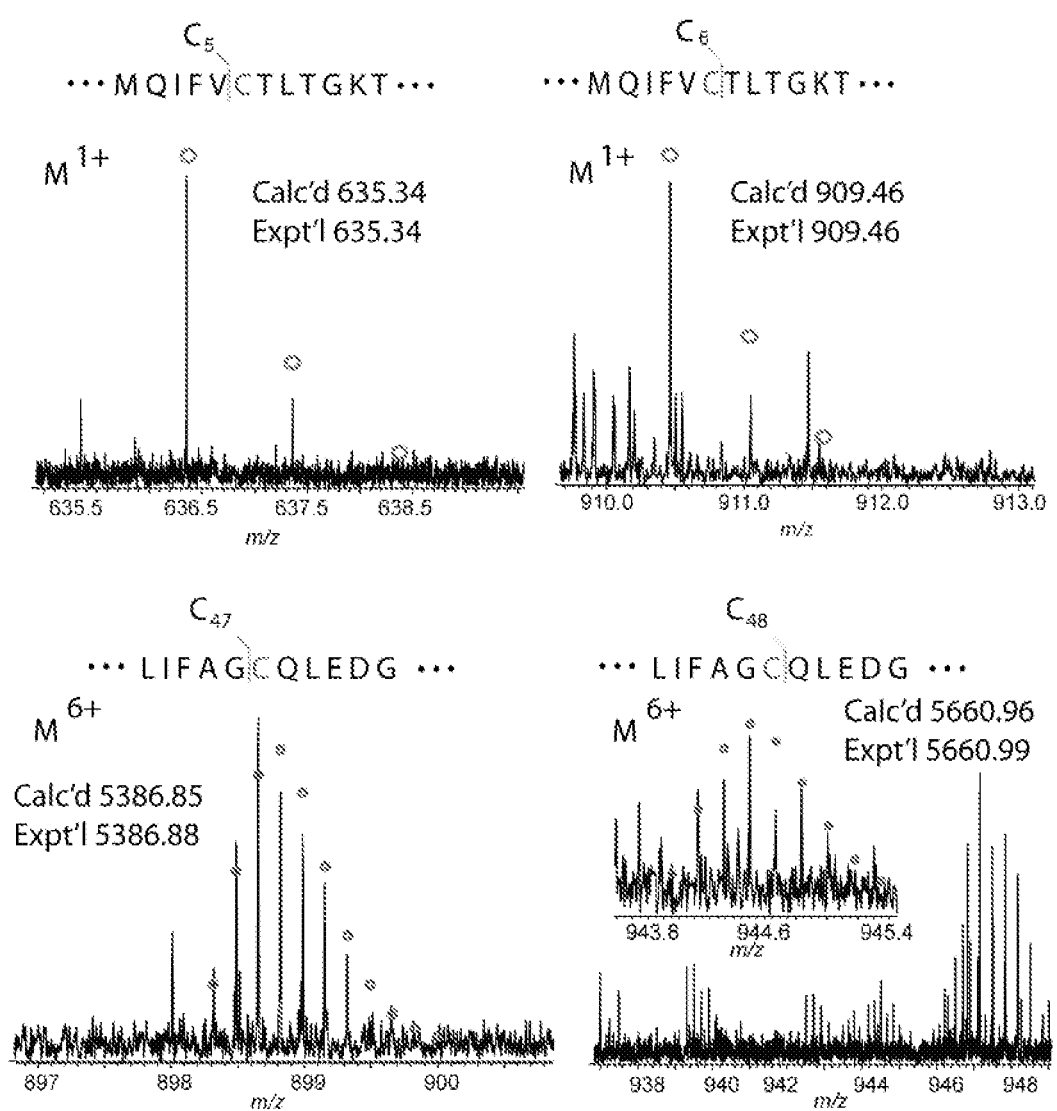

FIG. 12. Key ECD fragment ions for K6C, K48C-linked trimer, according to the Examples. Circles represent theoretical isotopic abundance distribution of the isotopomer peaks. Calc'd: calculated most abundant molecular weight. Exp'l: experimental most abundant molecular weight. FIG. 12 discloses SEQ ID NOS 89, 89, 92 and 92, respectively, in order of appearance.

Figure 13:
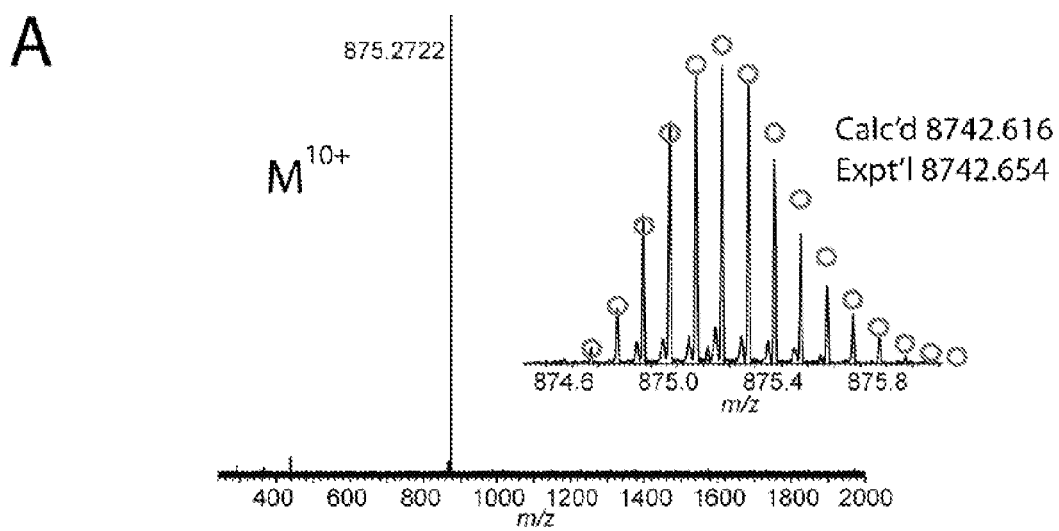

FIG. 13. ECD analysis of K11C, K48C-linked trimer, according to the Examples. (A) K11C, K48C-linked $Ub_{1-74}$ GlyGlyAA$_2$ parent ion isolation ($M^{10+}$ charge state) with insert of isotopomers. (B) Map of observed fragments. Data analysis for the map on the top (core peptide disclosed as SEQ ID NO: 93) includes the Nϵ-Gly-L-homothiaLys thioether linker modification at cysteine-11 and cysteine-48 (red) in c and z* ion predictions. Bottom map (SEQ ID NO: 93) does not include thioether linker modifications in the sequence.

Figure 14:
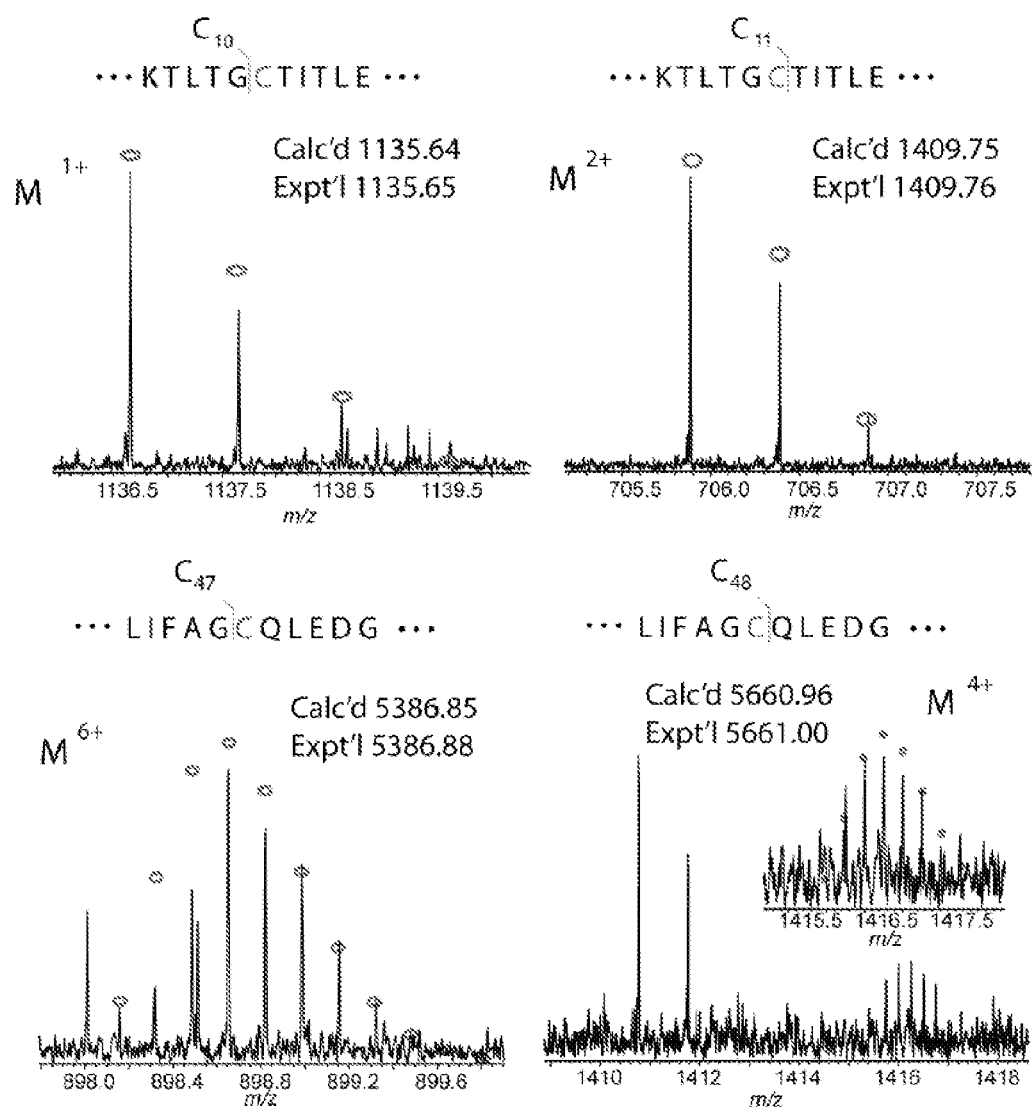

FIG. 14. Key ECD fragment ions for K11C, K48C-linked trimer. Circles represent theoretical isotopic abundance distribution of the isotopomer peaks. Calc'd: calculated most abundant molecular weight. Exp'l: experimental most abundant molecular weight. FIG. 14 discloses SEQ ID NOS 94, 94, 92 and 92, respectively, in order of appearance.

Figure 15:
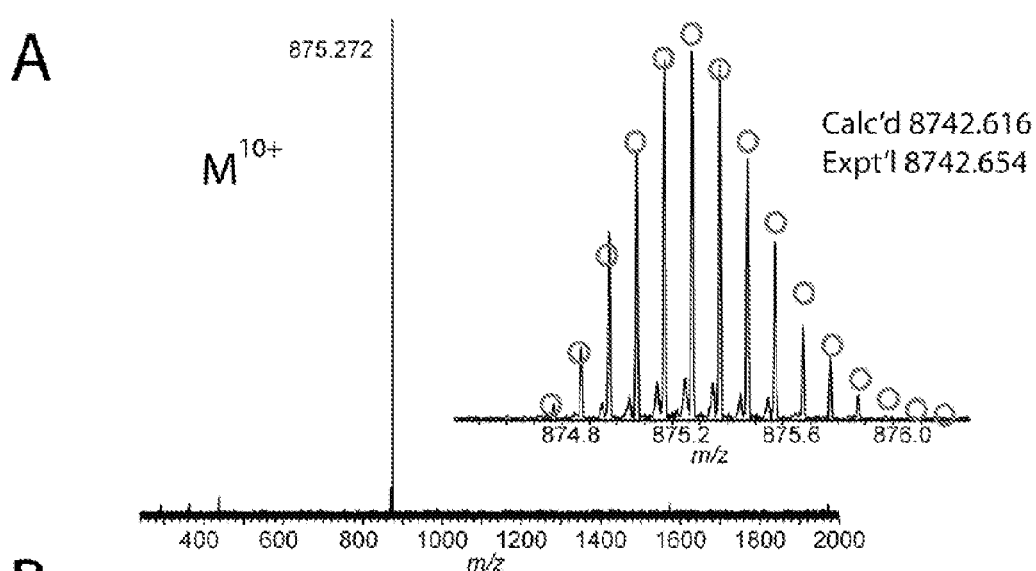
Figure 15:
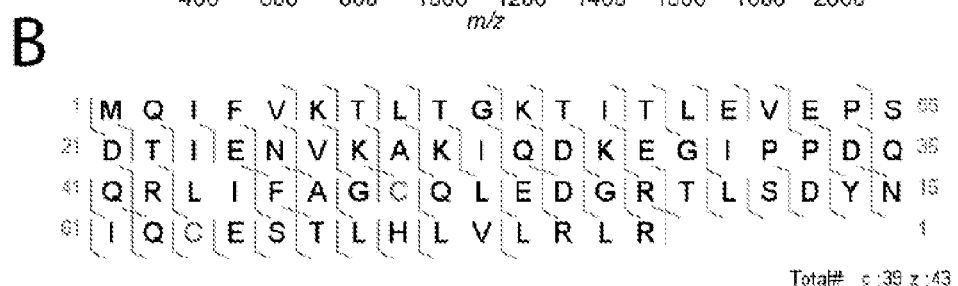
Figure 15:
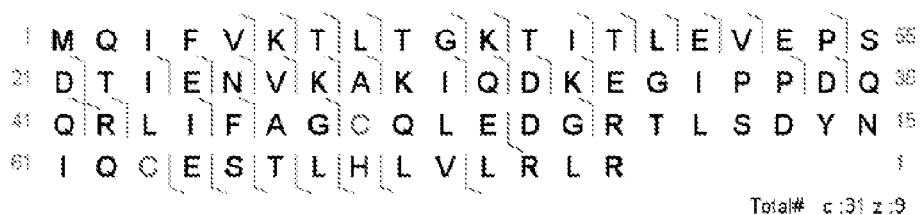

FIG. 15. ECD analysis of K48C, K63C-linked trimer, according to the Examples. (A) K48C, K63C-linked $Ub_{1-74}$ GlyGlyAA$_2$ parent ion isolation ($M^{10+}$ charge state) with insert of isotopomers. (B) Map of observed fragments. Data analysis for the map on top (core peptide disclosed as SEQ ID NO: 95) includes the Nϵ-Gly-L-homothiaLys thioether linker modification at cysteine-48 and cysteine-63 (red) in c and z* ion predictions. Bottom map (SEQ ID NO: 95) does not include thioether linker modifications in theoretical analysis.

Figure 16:
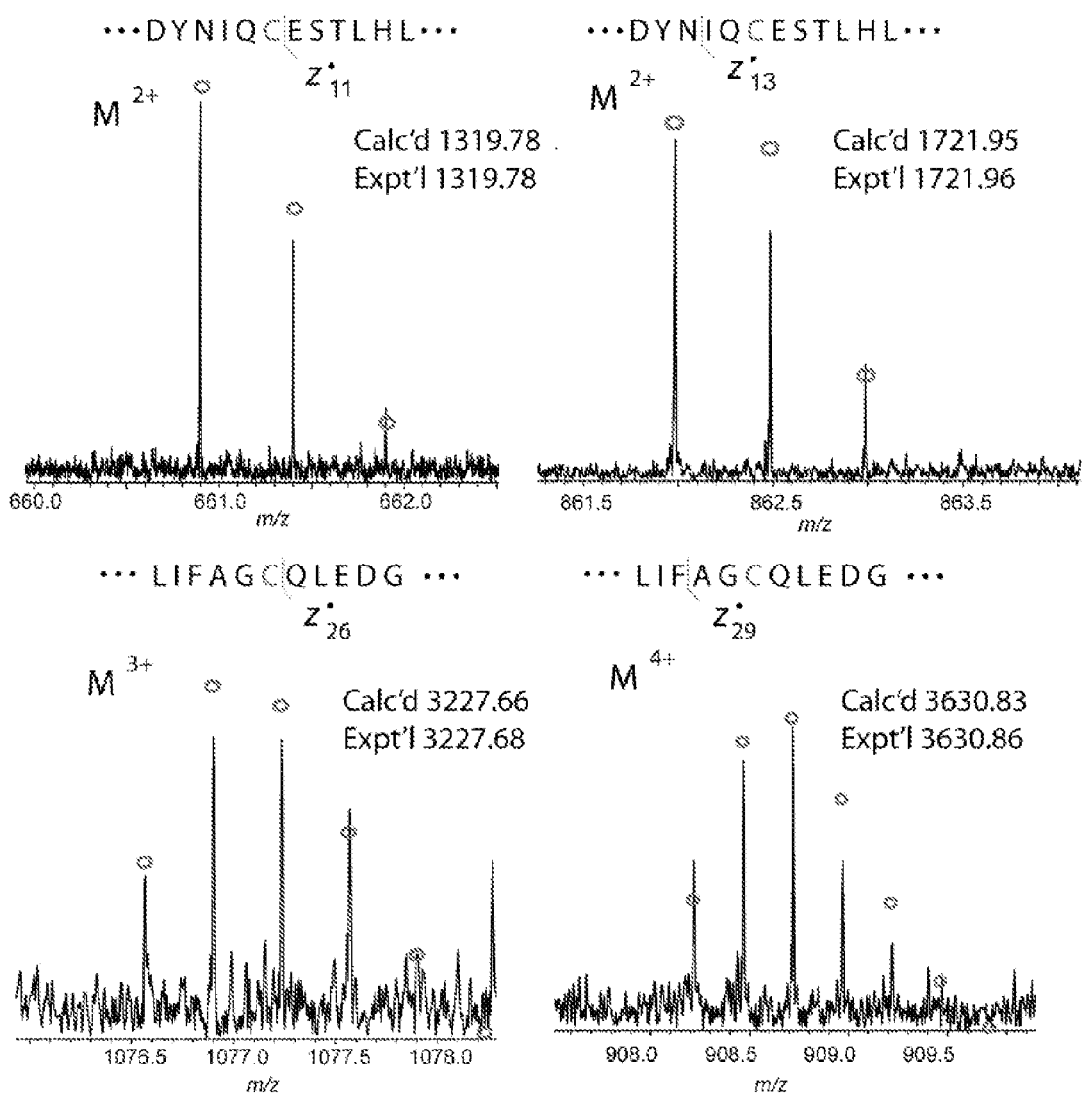

FIG. 16. Key ECD fragment ions for K48C, K63C-linked trimer, according to the Examples. Circles represent theoretical isotopic abundance distribution of the isotopomer peaks. Calc'd: calculated most abundant molecular weight. Exp'l: experimental most abundant molecular weight. FIG. 16 discloses SEQ ID NOS 96, 96, 92 and 92, respectively, in order of appearance.

Figure 17:
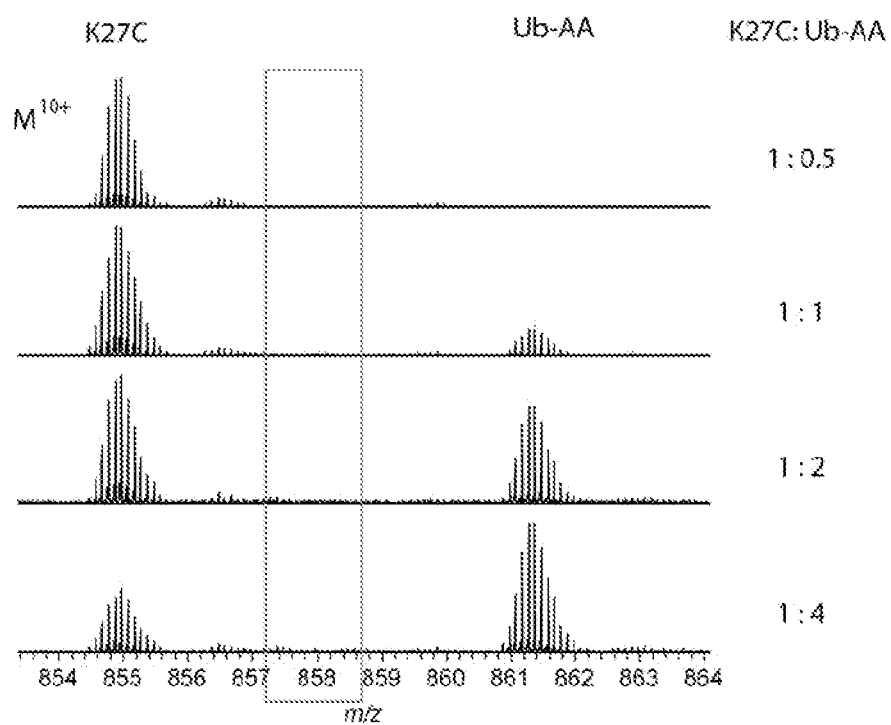

FIG. 17. High resolution FT-ICR MS analysis of K27C-linked dimer with varying amounts of Ub-AA, according to the Examples. Relative amounts of Ub-AA to UbK27C are shown on the right. Box shows where $M^{20+}$ dimer should appear.

Figure 18:
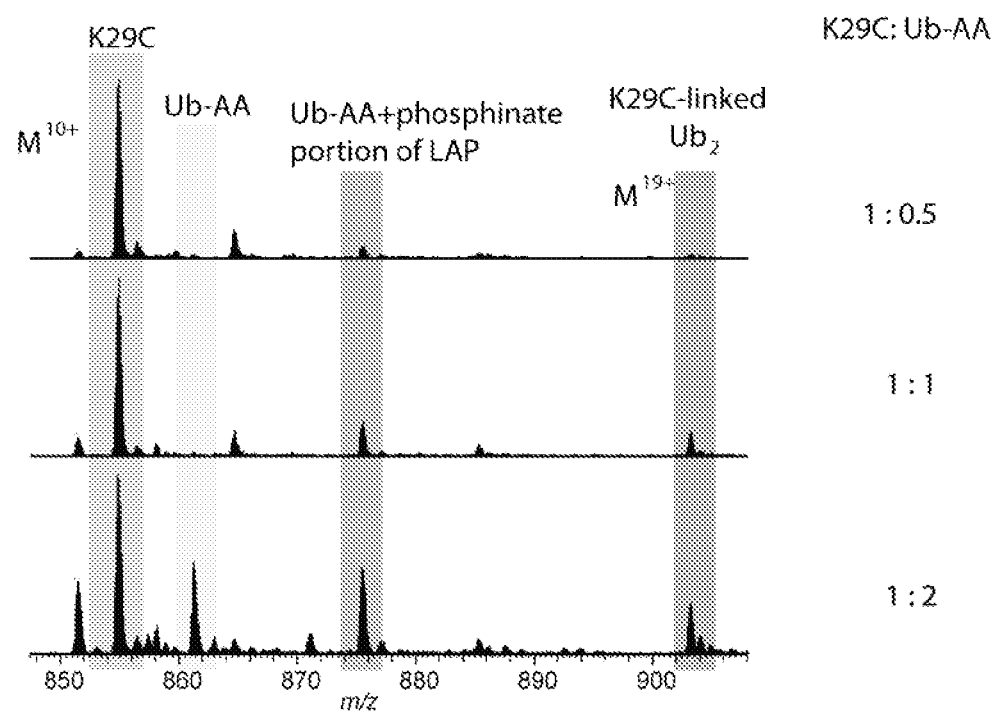

FIG. 18. FT-ICR analysis of K29C-linked dimer with varying amounts of Ub-AA, according to the Examples. The purple box highlights the formation of the desired dimer. Relative concentrations of Ub-AA to UbK29C are shown on the right.

Figure 19:
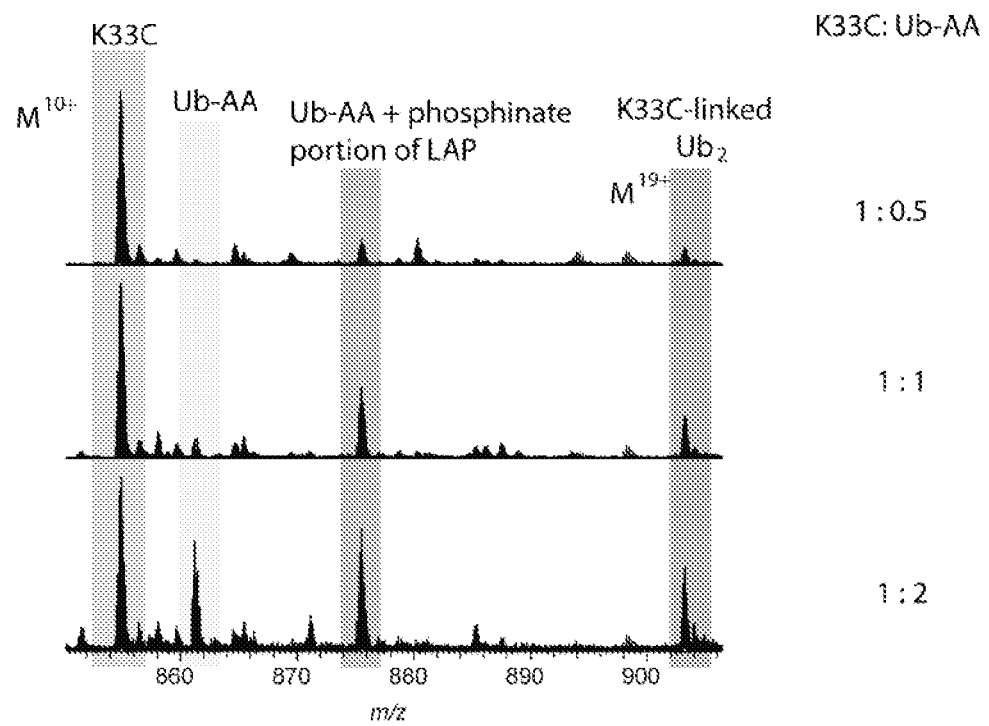

FIG. 19. High resolution FT-ICR MS analysis of K33C-linked dimer with varying amounts of Ub-AA, according to the Examples. The purple box highlights the formation of the desired dimer. Relative concentrations of Ub-AA to UbK33C are shown on the right.

Figure 20:
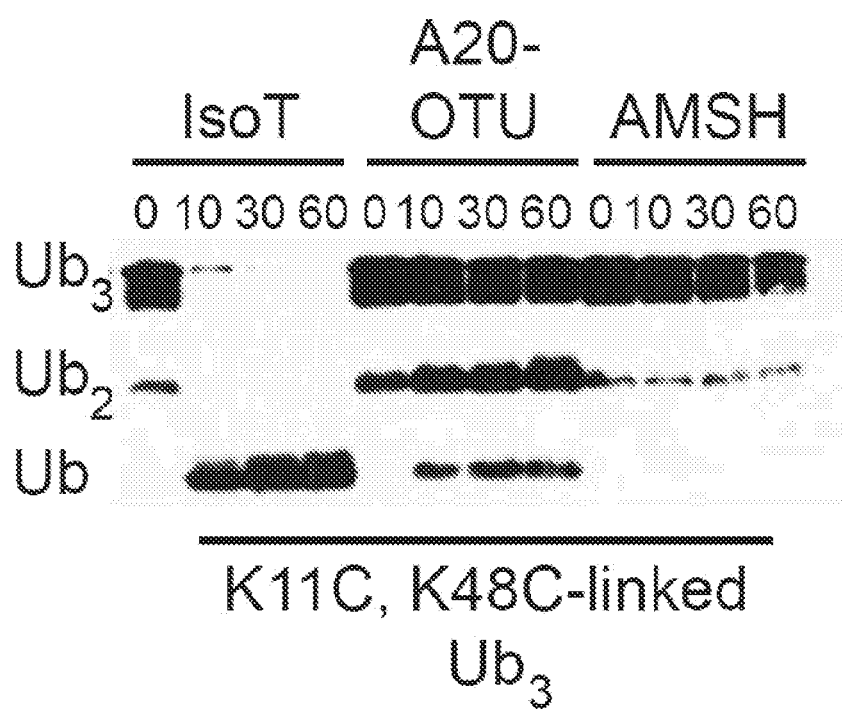

FIG. 20. Hydrolytic cleavage of K11C, K48C-linked Ub trimer with IsoT, A20-OUT, and AMSH, according to the Examples.

Figure 21:
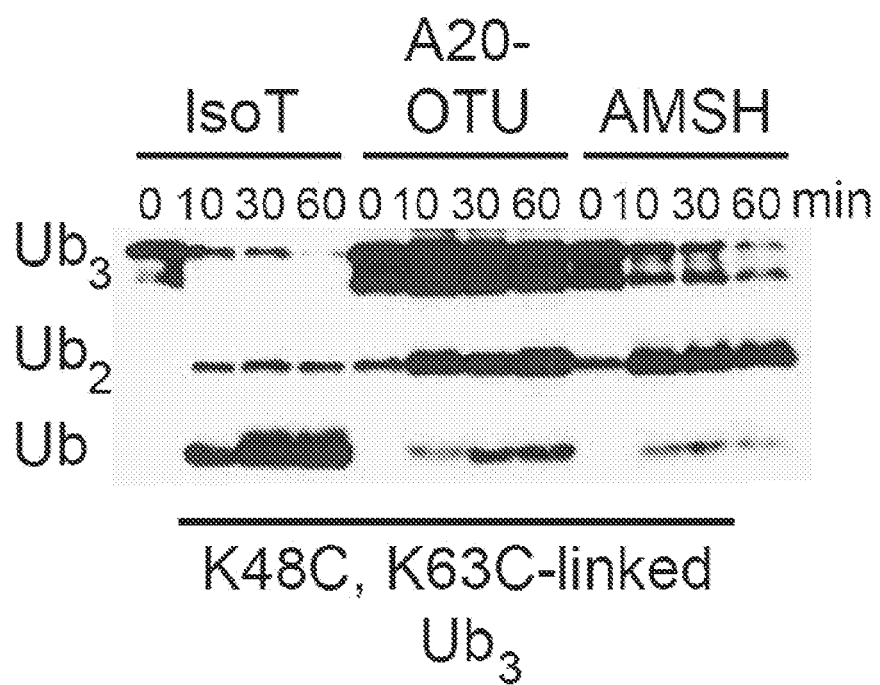

FIG. 21. Hydrolytic cleavage of K48C, K63C-linked Ub trimer with IsoT, A20-OUT, and AMSH, according to the Examples.

Figure 22:
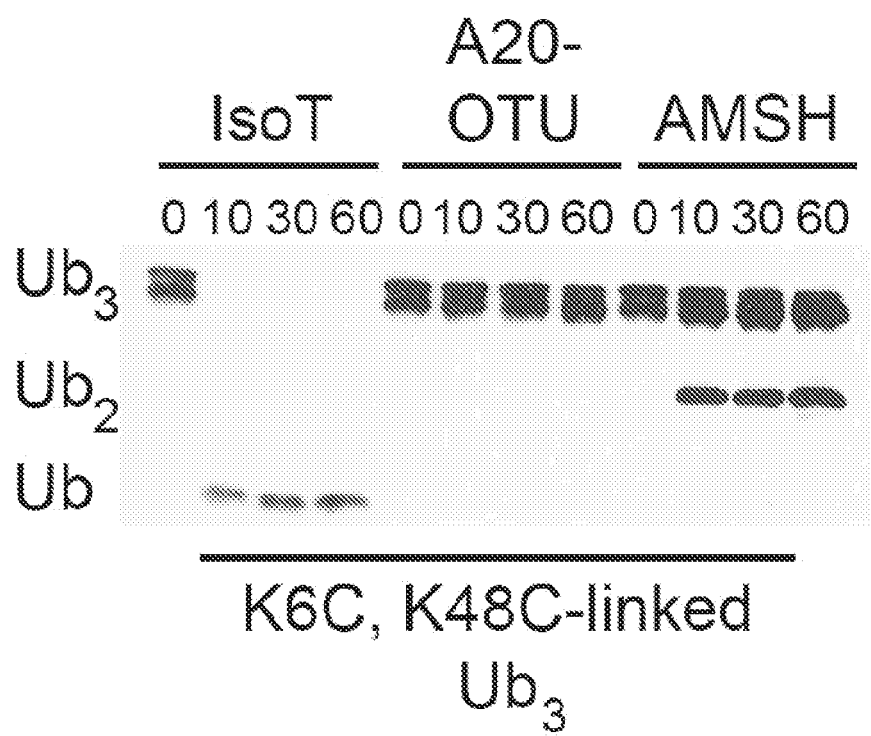

FIG. 22. Hydrolytic cleavage of K6C, K48C-linked Ub trimer with IsoT, A20-OUT, and AMSH, according to the Examples.

Figure 23:
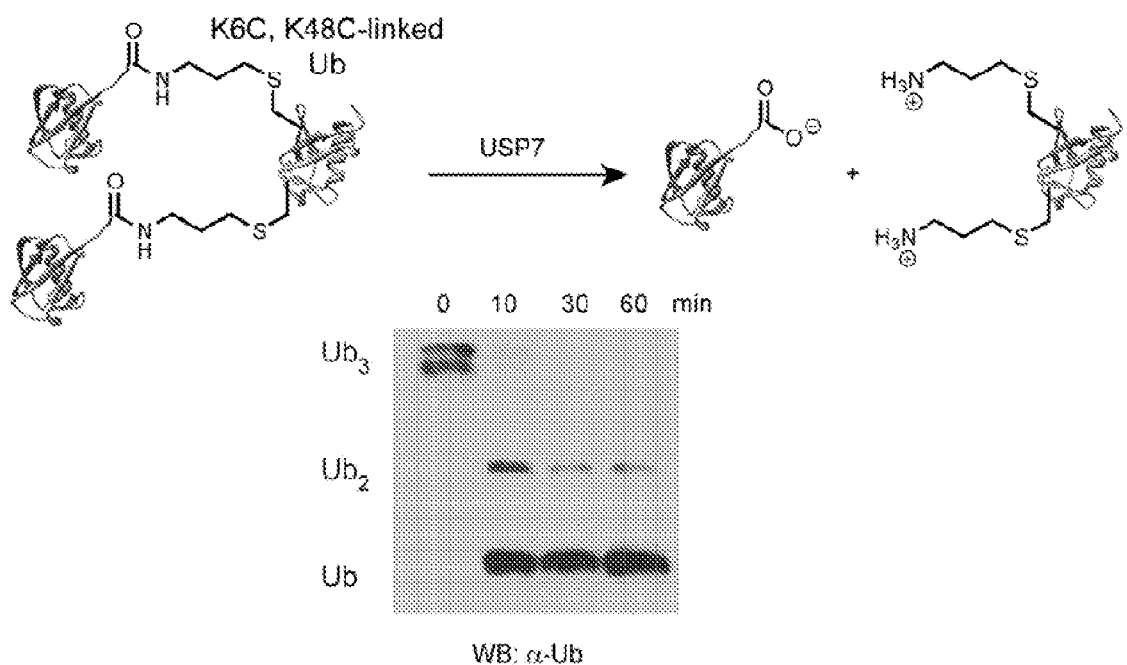

FIG. 23. Hydrolytic cleavage of K6C, K48C-linked Ub trimer with USP7, according to the Examples.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include the plural reference. Thus, for example, a reference to "a protein" is a reference to one or more proteins.

Alkyl groups include straight chain and branched alkyl groups having from 1 to 20 carbon atoms or, in some embodiments, from 1 to 12, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed below. For example, the term haloalkyl refers to an alkyl group substituted with one or more halogen atoms.

Alkenyl groups include straight and branched chain alkyl and cycloalkyl groups in which at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, among others. Representative substituted alkenyl groups may be mono-substituted or substituted more than once, such as, but not limited to, mono-, di- or tri-substituted with substituents such as those listed below.

The term "alkylene" alone or as part of another substituent refers to a divalent radical of an alkyl (including cycloalkyl) group. Each alkylene may be divalent at the same carbon or different carbons. Thus, e.g., the alkylene group based on ethyl is ethylene, and includes —CH(CH$_3$)— as well as —CH$_2$CH$_2$—. For alkylene groups, no particular pattern of attachment or orientation of the group is implied.

Alkylene oxide is an alkylene group in which one or more carbon atoms have been replaced with oxygen such that the resulting group is chemically stable. Nonlimiting examples of alkylene oxide groups include polyethylene glycol, polypropylene glycol, polytetramethylene oxide and the like.

Aryl groups are cyclic aromatic hydrocarbons having 6-14 carbons and that do not contain heteroatoms. Aryl groups include monocyclic, bicyclic and tricyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-12 carbons, and in others from 6-10 or even 6-8 carbon atoms in the ring portions of the groups. The phrase "aryl groups" further includes groups containing fused rings, such as fused aromatic-aliphatic ring systems (e.g., indanyl, tetrahydronaphthyl, and the like). However, it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed below.

The term "arylene" or "aralkylene" alone or as part of another substituent refers to a divalent radical of an aryl or aralkyl group. Each arylene or aralkylene will be divalent at different carbons of the aromatic ring or, in the case of aralkylene, may be divalent at the same carbon or different carbons of the alkylene portion. Further the alkylene portion of aralkylene may be a single chain or two separate chains attached to different carbons of the aromatic group. Thus, examples of arylene and aralkylene include but are not limited to phenylene, benzylene, ethylphenylethylene and the like. No particular pattern of attachment or orientation of the arylene or aralkylene group is implied.

In general, "substituted" refers to a group, as defined above (e.g., an alkyl or aryl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls: alkoxy, alkenoxy, alkynoxy, aryloxy, aralkyloxy, heterocyclyloxy, and heterocyclylalkoxy groups; carbonyls(oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; inines; nitro groups; nitriles (i.e., CN); and the like.

As used herein, the terms "sequence identity" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (See, e.g., NCBI web site). Such sequences are then said to be "substantially identical." This term also refers to, or can be applied to, the complement of a test sequence. The term also includes sequences that have deletions and/or additions, as well as those that have substitutions. Typically, identity exists over a region that is at least about 25 amino acids or nucleotides in length, or more preferably over a region that is at least 50-100 amino acids or nucleotides in length.

As used herein, the terms "polypeptide", "peptide" and "protein" are used interchangeably herein to mean a polymer comprising two or more amino acids joined to each other by peptide bonds or modified peptide bonds. Polypeptide refers to both short chains, commonly referred to as peptides or oligomers, and to longer chains, generally referred to as proteins. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the terms "variant" or "mutant" are used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form. Such changes include, but are not limited to: changes in one, few, or even several amino acid side chains; changes in one, few or several amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A "variant" or "mutant" can have either enhanced, decreased, changed, or substantially similar properties as compared to the naturally occurring protein or peptide. In one embodiment, a variant of Ub or Ubl is a substrate for a deubiquitinating enzyme or for a ubiquitin binding protein.

As used herein, the term "oligomer" refers to a short polymer composed of two or more monomers, e.g., 2, 3, 4, 5, 6, 7, 8, 9, 10, 15, 20, 25, 30, 35, 40, or 50 monomers or a range of monomers between and including any two of these values.

As used herein, reference to an ubiquitin (Ub) protein or polypeptide or ubiquitin-like (Ubl) protein or polypeptide, including an isolated Ub or Ubl, includes full-length proteins, fusion proteins, or any fragment, mutant, variant, or homologue of such a protein. Such a Ub or Ubl protein can include, but is not limited to, purified Ub or Ubl protein, recombinantly produced Ub or Ubl protein, soluble Ub or Ubl protein, insoluble Ub or Ubl protein, and isolated Ub or Ubl protein associated with other proteins, and isolated Ub or Ubl associated with cellular membranes. An isolated protein is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Typically, an isolated Ub or Ubl polypeptide is produced recombinantly.

In addition, and by way of example, a "human Ub protein" refers to a Ub protein from a human (*Homo sapiens*) or to a Ub protein that has been otherwise produced from the knowledge of the structure (e.g., sequence) and perhaps the function of a naturally occurring Ub protein from *Homo sapiens*. In other words, a human Ub protein includes any Ub protein that has substantially similar structure and function of a naturally occurring Ub protein from *Homo sapiens* or that is a biologically active (i.e., has biological activity) homologue of a naturally occurring Ub protein from *Homo sapiens* as described in detail herein. As such, a human Ub protein can include purified, partially purified, recombinant, mutated/modified and synthetic proteins. According to the present invention, the terms "modification" and "mutation" can be used interchangeably, particularly with regard to the modifications/mutations to the amino acid sequence of Ub (or nucleic acid sequences) described herein. The amino acid sequence of human Ub is 76 amino acids in length and is a post-translational modification of the full-length translational product of human Ub (Genbank Accession No. CAA44911.1). Human Ub is set forth below as SEQ ID NO: 1.

```
                                                         (SEQ ID NO: 1)
  1 MQIFVKTLTG KTITLEVEPS DTIENVKAKI QDKEGIPPDQ QRLIFAGKQL EDGRTLSDYN

61 IQKESTLHLV LRLRGG
```

A number of proteins also modify the ε-amino group in proteins analogously to ubiquitin, but function in distinct signaling pathways. These proteins are known as ubiquitin-like proteins (Ubl). Oligomers of Ubl may be constructed as disclosed herein. Ubl include but are not limited to SUMO1, SUMO2, SUMO3 and ISG15. Sequences of these proteins are set forth below as SEQ ID NOS:2, 3, 4, and 5, respectively.

```
SUMO 1, GenBank Accession No. AAC50996.1
                                                         (SEQ ID NO: 2)
  1 MSDQEAKPST EDLGDKKEGE YIKLKVIGQD SSEIHFKVKM TTHLKKLKES YCQRQGVPMN

61 SLRFLFEGQR IADNHTPKEL GMEEEDVIEV YQEQTGGHST V

SUMO 2, GenBank Accession No. P61956.3
                                                         (SEQ ID NO: 3)
  1 MADEKPKEGV KTENNDHINL KVAGQDGSVV QFKIKRHTPL SKLMKAYCER QGLSMRQIRF

61 RFDGQPINET DTPAQLEMED EDTIDVFQQQ TGGVY

SUMO 3, GenBank Accession No. P55854.2
                                                         (SEQ ID NO: 4)
  1 MSEEKPKEGV KTENDHINLK VAGQDGSVVQ FKIKRHTPLS KLMKAYCERQ GLSMRQIRFR

61 FDGQPINETD TPAQLEMEDE DTIDVFQQQT GGVPESSLAG HSF

ISG15, GenBank Accession No. AAH09507.1
                                                         (SEQ ID NO: 5)
  1 MGWDLTVKML AGNEFQVSLS SSMSVSELKA QITQKIGVHA FQQRLAVHPS GVALQDRVPL

61 ASQGLGPGST VLLVVDKCDE PLNILVRNNK GRSSTYEVRL TQTVAHLKQQ VSGLEGVQDD

121 LFWLTFEGKP LEDQLPLGEY GLKPLSTVFM NLRLRGGGTE PGGRS
```

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Homologues or variants of Ub or Ubl can be produced that contain one or more conservative or non-conservative amino acid changes, compared with the native enzyme, so long as the sterol binding or cholesterol incorporation activity is retained. Typically, variants have at least 50%, at least 60%, at least 70%, at least 80%, or at least 90% amino acid sequence identity compared to the original sequences such as any one of SEQ ID NOs: 1, 2, 3, 4, or 5. In some embodiments, high sequence identity variants are provided in which the amino acid sequence identity of the variant to the Ub or Ubl is at least 95%, at least 96%, at least 97%, at least 98% or even at least 99%. In other embodiments, Ub or Ubl variants include 1, 2, 3, 4, 5, 6, 7, 8, 9, 10, or more conservative or nonconservative amino acid substitutions such as 15, 20, 25, 30, or even 40 amino acid substitutions so long as cholesterol incorporation activity is retained. The ability of variants of Ub or Ubl to serve as substrates for deubiquitination can be determined using a standard activity assay, such as the assay described in the Examples.

Conservative variants can be obtained that contain one or more amino acid substitutions of, e.g., SEQ ID NO: 1, in which an alkyl amino acid is substituted for an alkyl amino acid in the Ub or Ubl amino acid sequence, an aromatic amino acid is substituted for an aromatic amino acid in Ub or Ubl amino acid sequence, a sulfur-containing amino acid is substituted for a sulfur-containing amino acid in the Ub or Ubl amino acid sequence, a hydroxy-containing amino acid is substituted for a hydroxy-containing amino acid in the Ub or Ubl amino acid sequence, an acidic amino acid is substituted for an acidic amino acid in the Ub or Ubl amino acid sequence, a basic amino acid is substituted for a basic amino acid in the Ub or Ubl amino acid sequence, or a dibasic monocarboxylic amino acid is substituted for a dibasic monocarboxylic amino acid in the Ub or Ubl amino acid sequence.

Among the common amino acids, for example, a "conservative amino acid substitution" is illustrated by a substitution among amino acids within each of the following groups: (1) glycine, alanine, (2) valine, leucine, and isoleucine, (3) phenylalanine, tyrosine, and tryptophan, (4) cysteine and methionine, (5) serine and threonine. (6) aspartate and glutamate, (7) glutamine and asparagine, and (8) lysine, arginine and histidine.

Conservative amino acid changes in, e.g., the human Ub, can be introduced by substituting appropriate nucleotides for the nucleotides encoding SEQ ID NO: 1. Such "conservative amino acid" variants can be obtained, for example, by oligonucleotide-directed mutagenesis, linker-scanning mutagenesis, mutagenesis using the polymerase chain reaction, and the like. Ausubel et al., supra; Ausubel et al. (eds.), SHORT PROTOCOLS IN MOLECULAR BIOLOGY, 5th Edition, John Wiley & Sons, Inc. (2002). Also see generally, McPherson (ed.), DIRECTED MUTAGENESIS: A PRACTICAL APPROACH, IRL Press (1991). A useful method for identification of locations for sequence variation is called "alanine scanning mutagenesis" a described by Cunningham and Wells in *Science,* 244:1081-1085 (1989).

Ub or Ubl variants that contain one or more non-conservative amino acid substitutions, such as substitution of cysteine residues for one or more lysine residues in Ub or Ubl having any one of SEQ ID NOs: 1, 2, 3, 4 and 5 and that retain the ability to serve as a substrate for deubiquitination enzymes can also be produced and used as disclosed herein. Other non-conservative amino acid substitutions are known in the art and include, without limitation, leucine for aspartate or valine for threonine. Non-conservative variants can also include amino acid insertions as compared to the native sequence such as, without limitation, insertion of methionine. As will be appreciated by the skilled artisan, the same methods used for generating conservative variants may be adapted and used to produce nonconservative variants.

In addition, routine deletion analyses of DNA molecules can be performed to obtain "functional fragments" of Ub, Ubl or homologues thereof. The fragments are inserted into expression vectors in proper reading frame, and the expressed polypeptides are isolated and tested for the ability to incorporate cholesterol into lipid bilayers. One alternative to exonuclease digestion is to use oligonucleotide-directed mutagenesis to introduce deletions or stop codons to specify production of a desired fragment. Alternatively, particular fragments of the Ub or Ubl gene can be synthesized using the polymerase chain reaction. Standard techniques for functional analysis of proteins are described by, for example, Treuter et al., *Molec. Gen. Genet.,* 240:113 (1993); Content et al., "Expression and preliminary deletion analysis of the 42 kDa 2-5A synthetase induced by human interferon," in BIOLOGICAL INTERFERON SYSTEMS, PROCEEDINGS OF ISIR-TNO MEETING ON INTERFERON SYSTEMS, Cantell (ed.), pages 65-72 (Nijhoff 1987); Herschman, "The EGF Receptor," in CONTROL OF ANIMAL CELL PROLIFERATION, Vol. 1, Boynton et al., (eds.) pages 169-199 (Academic Press 1985); Coumailleau et al., *J. Biol. Chem.,* 270:29270 (1995); Fukunaga et al., *J. Biol. Chem.,* 270:25291 (1995); Yanmaguchi et al., *Biochem. Pharmacol.* 50:1295 (1995); and Meisel et al., *Plant Molec. Biol.,* 30:1 (1996). In some embodiments the functional fragment retains at least 50% or at least 60% of the amino acids of the native sequence. In others the functional fragment retains at least 70%, at least 80%, at least 90%, at least 95%, at least 98% or at least 99% of the amino acids of the native sequence.

In one aspect, the present technology provides well-defined oligomers of ubiquitin and ubiquitin-like polypeptides. Such oligomers may be used as tools for probing the manifold roles of ubiquitination in cellular physiology and human diseases. The present oligomers include two or more monomers wherein each monomer is independently selected from a ubiquitin polypeptide or a ubiquitin-like polypeptide. The monomers are covalently linked to each other via a thioether group or groups. Typically, each thioether group links the peptide backbone of one monomer to the carboxy terminus of another monomer. For example, each thioether group may include a cysteine residue of one of the monomers. Thus, an oligomer may be constructed wherein each monomer is a mutant in which each cysteine residue in the thioether group replaces a lysine residue in the native sequence of the monomer.

Oligomers of the present technology may include various numbers of monomers such as, for example, 2, 3, 4, 5, 6, 7, 8, 9 or 10 monomers. The oligomers may be linear or branched. Linear oligomers, other than dimers, include one or more internal monomers that are each linked to 2 monomers: one through a thioether group attached to the peptide backbone of the internal monomer and one through a thioether group attached to the carboxy terminus of the internal monomer.

In contrast to linear oligomers, a branched oligomer includes at least 3 monomers. At least one monomer (the internal monomer) of the branched oligomer is covalently linked to at least 2 other monomers via thioether groups to the peptide backbone of the internal monomer. In some embodiments, the thioether groups of at least two monomers include cysteines at different positions within the monomer. For example, for ubiquitin, the internal monomer may include a thioether group at K6C and a thioether group at K48C, or at K11C and K48C, or at K48C and K63C.

Oligomers of the present technology may incorporate any Ub or Ubl monomers, including mutants, variants, homologues and fragments of any of the foregoing. As described further below, the monomers may or may not include an alkene attached to the carboxy terminus. In some embodiments, each monomer of the oligomer is independently selected from a polypeptide that
   a. has at least 95% sequence identity to a sequence selected from the group consisting of SEQ ID NOS:1, 2, 3, 4, and 5;
   b. comprises a sequence that has at least 95% sequence identity to a sequence selected from the group consisting of SEQ ID NOS: 1, 2, 3, 4, and 5; or
   c. is a fragment of a polypeptide having at least 95% sequence identity to a sequence selected from the group consisting of SEQ ID NOS:1, 2, 3, 4, and 5, wherein the ubiquitin or ubiquitin-like polypeptide is a substrate for a deubiquinating enzyme or for proteins containing ubiquitin-binding domains, (e.g., RPN10, RPN13, hHR23A, Dsk2, p62, NBR1, RAP80, NEMO, TAB2, TAB3, and A20) when covalently attached via its carboxy terminus to another protein.

Examples of mutant Ub and Ubl in which one or more lysine residues are replaced with cysteine residues are set forth for SEQ ID NO:1 in Table 1 and for SEQ ID NO:3 in Table 2. The asterisk (*) indicates presence of the specified mutation. Those skilled in the art will understand that any of these mutants may be further modified to include a C-terminal alkene as described herein.

TABLE 1

Mutants of SEQ ID NO: 1

| Mutant No. | SEQ ID NO: | K6C | K11C | K27C | K29C | K33C | K48C | K63C |
|---|---|---|---|---|---|---|---|---|
| 1 | 6 | * | | | | | | |
| 2 | 7 | | * | | | | | |
| 3 | 8 | | | * | | | | |
| 4 | 9 | | | | * | | | |
| 5 | 10 | | | | | * | | |
| 6 | 11 | | | | | | * | |
| 7 | 12 | | | | | | | * |
| 8 | 13 | * | * | | | | | |
| 9 | 14 | * | | * | | | | |
| 10 | 15 | * | | | * | | | |
| 11 | 16 | * | | | | * | | |
| 12 | 17 | * | | | | | * | |
| 13 | 18 | * | | | | | | * |
| 14 | 19 | | * | * | | | | |
| 15 | 20 | | * | | * | | | |
| 16 | 21 | | * | | | * | | |
| 17 | 22 | | * | | | | * | |
| 18 | 23 | | * | | | | | * |
| 19 | 24 | | | * | * | | | |
| 20 | 25 | | | * | | * | | |
| 21 | 26 | | | * | | | * | |
| 22 | 27 | | | * | | | | * |
| 23 | 28 | | | | * | * | | |
| 24 | 29 | | | | * | | * | |
| 25 | 30 | | | | * | | | * |
| 26 | 31 | | | | | * | * | |
| 27 | 32 | | | | | | * | * |
| 28 | 33 | | | | | | * | * |
| 29 | 34 | * | * | * | | | | |
| 30 | 35 | * | * | | * | | | |
| 31 | 36 | * | * | | | * | | |
| 32 | 37 | * | * | | | | * | |
| 33 | 38 | * | * | | | | | * |
| 34 | 39 | * | | * | * | | | |
| 35 | 40 | * | | * | | * | | |
| 36 | 41 | * | | * | | | * | |
| 37 | 42 | * | | * | | | | * |
| 38 | 43 | * | | | * | * | | |
| 39 | 44 | * | | | * | | * | |
| 40 | 45 | * | | | * | | | * |
| 41 | 46 | * | | | | * | * | |
| 42 | 47 | * | | | | * | | * |
| 43 | 48 | * | | | | | * | * |
| 44 | 49 | | * | * | * | | | |
| 45 | 50 | | * | * | | * | | |
| 46 | 51 | | * | * | | | * | |
| 47 | 52 | | * | * | | | | * |
| 48 | 53 | | * | | * | * | | |
| 49 | 54 | | * | | * | | * | |
| 50 | 55 | | * | | * | | | * |
| 51 | 56 | | * | | | * | * | |
| 52 | 57 | | * | | | | * | * |
| 53 | 58 | | * | | | | * | * |
| 54 | 59 | | | * | * | * | | |
| 55 | 60 | | | * | * | | * | |
| 56 | 61 | | | * | * | | | * |
| 57 | 62 | | | * | | | * | * |
| 58 | 63 | | | * | | | * | * |
| 59 | 64 | | | * | | | * | * |
| 60 | 65 | | | | * | * | * | |
| 61 | 66 | | | | * | * | | * |
| 62 | 67 | | | | * | | * | * |
| 63 | 68 | | | | | * | * | * |

TABLE 2

Mutants of SEQ ID NO: 3

| Mutant No. | SEQ ID NO: | K11C | K21C | K33C | K42C | K45C |
|---|---|---|---|---|---|---|
| 1 | 69 | * | | | | |
| 2 | 70 | | * | | | |
| 3 | 71 | | | * | | |
| 4 | 72 | | | | * | |
| 5 | 73 | | | | | * |
| 6 | 74 | * | * | | | |
| 7 | 75 | * | | * | | |
| 8 | 76 | * | | | * | |
| 9 | 77 | * | | | | * |
| 10 | 78 | | * | * | | |

TABLE 2-continued

Mutants of SEQ ID NO: 3

| Mutant No. | SEQ ID NO: | K11C | K21C | K33C | K42C | K45C |
|---|---|---|---|---|---|---|
| 11 | 79 |  | * |  | * |  |
| 12 | 80 |  | * |  |  | * |
| 13 | 81 |  |  | * | * |  |
| 14 | 82 |  |  | * |  | * |
| 15 | 83 |  |  |  | * | * |

In another aspect, the present technology provides building blocks for constructing the oligomers described herein. One such building block is a ubiquitin or ubiquitin-like polypeptide that includes a carboxy terminal alkenyl group. In some embodiments, a cysteine residue replaces at least one lysine residue in the ubiquitin or ubiquitin-like polypeptide to provide a mutant Ub or Ubl bearing a C-terminal alkene group. As in the oligomers, the ubiquitin or ubiquitin-like polypeptide building block may be a polypeptide that
  a. has at least 95% sequence identity to a sequence selected from the group consisting of SEQ ID NOS:1, 2, 3, 4, and 5;
  b. comprises a sequence that has at least 95% sequence identity to a sequence selected from the group consisting of SEQ ID NOS:1, 2, 3, 4, and 5; or
  c. is a fragment of a polypeptide having at least 95% sequence identity to a sequence selected from the group consisting of SEQ ID NOS:1, 2, 3, 4, and 5, wherein the ubiquitin or ubiquitin-like polypeptide is a substrate for a deubiquinating enzyme when covalently attached via its carboxy terminus to another protein.

In some embodiments, the Ub or Ubl polypeptide building block is a mutant in which each of 1, 2 or 3 lysine residues of the native sequence is replaced with a cysteine residue. For example, the Ub or Ubl polypeptide building block may include 1, 2, or 3 mutations selected from K6C, K11C, K27C, K29C, K33C, K48C, and K63C of Ub and K11C, K21C, K33C, K42C, and K45C of SUMO2. Specific mutants suitable for use as a building block for the present oligomers are set forth in Table 1 and Table 2 above.

The alkenyl group at the carboxy terminus of the Ub and Ubl polypeptide may have a variety of structures to facilitate its attachment and/or coupling to form oligomers For example, the carboxy terminal alkenyl group of the Ub and Ubl polypeptide may have the structure: —NR$^1$(R$^2$)CH=CH$_2$, wherein R$^1$ is H or C1-4 alkyl group; and R$^2$ is a substituted or unsubstituted alkylene, alkylene oxide, arylene or aralkylene group. In some embodiments, R$^1$ is H. In others, R$^1$ is a methyl or ethyl group. In some embodiments, R$^2$ is unsubstituted, e.g, unsubstituted alkylene or alkylene oxide. In certain embodiments, the carboxy terminal alkenyl group has the structure: —NH(CH$_2$)$_n$CH=CH$_2$, wherein n is an integer from 0 to 10. In certain embodiments, n is 1 or 2 (i.e., allyl amine or butenyl amine). Aminoalkenes such as these may be attached to the Ub and Ubl polypeptides by using Ub C-terminal hydrolases under conditions (a large stoichiometric excess of aminoalkene) that promote amide bond formation rather than amide bond hydrolysis.

In still another aspect, the present technology provides a method of making an oligomer as described herein using one or more Ub and/or Ubl building blocks as described herein. The method includes coupling a first monomer to a second monomer under free radical conditions such that the first and second monomers are linked by a thioether group. The first monomer is selected from a ubiquitin or ubiquitin-like polypeptide that includes a carboxy terminal alkenyl group and the second monomer is selected from a ubiquitin or ubiquitin-like polypeptide comprising one or more cysteine residues. Thus, any of the above-described monomer/building blocks may be used in this method.

Typically, the coupling is carried out in an aqueous buffer (pH 4-6, preferably 5) at a temperature below room temperature, e.g., about 0 or 4° C. to about 15° C. The coupling may also be carried out in the presence of a free radical initiator, under. e.g., sufficient ultraviolet (UV) light to generate free radicals. Suitable wavelengths of UV light that may be used include 300 to 450 nm. In some embodiments a wavelength of about 365 nm is used. Examples of suitable free radical initiators include lithium acyl phosphinates and water soluble 2,2-dimethoxy-2-phenylacetophenones.

To prepare trimers and larger oligomers, additional coupling steps may be performed or multiple couplings may be performed simultaneously, depending on whether a linear or branched oligomer is desired. Thus, in one embodiment, the method the second monomer comprises a carboxy terminal alkenyl group and is coupled to a third monomer under free radical conditions to form a thioether group and the third monomer is selected from a Ub or Ubl polypeptide including one or more cysteine residues. Likewise, if the third monomer comprises a carboxy terminal alkene, an additional coupling to a fourth monomer comprising a cysteine is possible. In this way, linear oligomers of 4, 5, 6, 7, 8 or more monomers may be constructed. Mixed linear oligomers may be formed if the subsequent monomers have cysteines at different positions. Alternatively, the second monomer includes two cysteine residues, and the second monomer is coupled to a third monomer under free radical conditions to form a thioether group at each cysteine, wherein the third monomer comprises a carboxy terminal alkene group. Subsequently further oligomers may be coupled to this branched oligomer as above.

In another aspect, a conjugate of the present oligomers with other proteins is provided. Thus, the conjugates include an oligomer of Ub or Ubl as described herein, covalently attached to a non-ubiquitin or non-ubiquitin polypeptide. In such conjugates, the oligomer may be attached to the non-ubiquitin or non-ubiquitin-like polypeptide through the carboxy terminus of one of the monomers in the oligomer. The oligomer may be attached to the non-Ub and non-Ubl using enzyme-catalyzed ligation (see, e.g., C. M. Pickart and S. Raasi. "Controlled synthesis of polyubiquitin chains." *Meth. Enzymol.* 2005, 399, 21-36). Alternatively the same thiol-ene chemistry described for the preparation of the oligomers themselves may be used to prepare the conjugate. Thus, site-directed mutagenesis of a lysine to a cysteine in the protein of interest may be performed. Installation of the C-terminal alkene in an of the oligomers described herein is carried out as described herein. Finally, the thiol-ene reaction between the oligomer and the mutated protein may be performed as described herein.

In another aspect, methods of using the oligomers are provided. The methods include adding any of the oligomers described herein to cultured cells and determining the effects of the added oligomer(s) on the cultured cells. In some embodiments, the effects of the added oligomer(s) are determined with respect to one or more of protein expression, mRNA levels, or levels of cellular signaling molecules.

EXAMPLES

The present technology is further illustrated by the following examples, which should not be construed as limiting in any way.

Example 1

Ubiquitin (Ub) Cloning and Expression

Cloning.

Ubiquitin (1-76) (herein referred to as $Ub_{1-76}$) was purchased from Addgene and cloned into pET-22b using the forward primer ggcggtCATATGCAGATCTTCGTCAAG (SEQ ID NO: 84) and reverse primer ggcggtGCGGCCGCT-CAACCACCTCTTAGTCT (SEQ ID NO: 85) containing NdeI and NotI restrictions sites. Lysine-to-cysteine mutations (KxC; where x is the position within Ub primary sequence) were introduced using the mutagenesis technique of splice overlap extension (SOE).[1] Primers containing the TGC mutation were used to replace the respective codon for lysine. Aspartate 77 was encoded in the reverse primer to afford the clone for UbD77.

Expression.

All Ub variants were expressed and purified from Rosetta™ 2(DE3)pLysS cells (Novagen) following a procedure adapted from Pickart 2005.[2] A starter culture was inoculated (10 mL LB media, 100 ug/mL Anmpicillin), grown to $OD_{600}$=0.5, and kept at 4° C. overnight. The starter culture was added to 1 L 2×YT media (16 g Peptone, 5 g NaCl, 10 g Yeast extract, 100 mg/ml Ampicilin) and grown at 37° C. Cultures were then induced with 0.4 mM IPTG at $OD_{600}$=0.6 and incubated for an additional 4 hours at 37° C. Cells were pelleted and resuspended in 150 mL lysis buffer (50 mM Tris pH 7.5, 0.5 mM EDTA, 1 mM EgTA, 0.02% Igepal, 1 mM PMSF, 1 mM DTT). After sonication, the lysate was clarified by centrifugation at 8,000 rpm for 30 min. Perchloric acid (70%, 0.19 mL) was added dropwise to the soluble layer and stirred for 20 min to precipitate impurities. After centrifuging at 8,000 rpm for 30 min, the supernatant was exchanged into FPLC Buffer A (50 mM $NH_4OAc$ pH 4.4, 1 mM EDTA, 1 mM DTT) with 2 rounds of dialysis (3.5 kD molecular weight cutoff snake-skin tubing). Ub variants were further purified by cation exchange chromatography with a gradient of 0% to 60% Buffer B (50 mM $NH_4OAc$ pH 4.4, 1 mM EDTA, 1 mM DTT, 1 M NaCl) over 35 column volumes. Fractions containing Ub (monitored by SDS-PAGE) were combined, concentrated, exchanged into $H_2O$ and lyophilized: the purpose of which is to determine yields and minimize variation in the concentration of stock solutions.

Example 2

Yeast Ub Hydrolase 1 (YUH1) Expression and Purification

YUH1 in pET-3a was purchased from Addgene and expressed from Rosetta™ 2(DE3)pLysS cells (Novagen). A starter culture was inoculated (10 mL LB media, 100 ug/mL ampicillin), grown at 37° C. for 6 h, and stored at 4° C. overnight. 1 L of LB was inoculated with starter culture and grown to $OD_{600}$=0.8. A culture was induced with 1 mM IPTG and grown 13 h at 18° C. Cells were harvested by centrifugation (8,000×g at 4° C., 30 min) and pellet was resuspended in lysis buffer (20 mM $NaPO_4$, 0.5 M NaCl, pH 7.4). Cells were lysed by sonication, and clarified by centrifugation (30,000×g at 4° C., 30 min). YUH1 was purified by ammonium sulfate precipitation. The 40% and 60% ammonium sulfate fraction was dialyzed into 25 mM NaCl, 50 mM HEPES pH 6.8, 1 mM DTT, and further purified by anion exchange (Buffer A: 25 mM Tris pH 8; Buffer B: 25 mM Tris pH 8, 1 M NaCl; 0-100% B, 30 column volumes).

Example 3

Synthesis of Ub Allyl Amine Adduct (Ub-AA)

Figure 1:
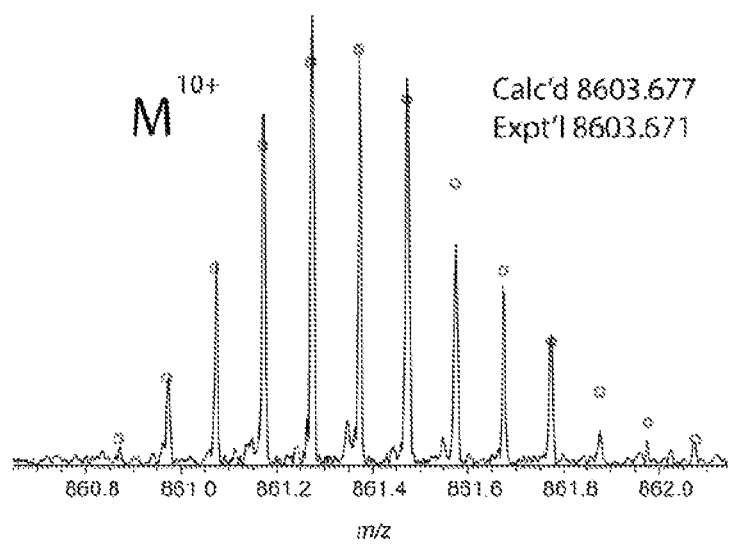
FIG. 1. High resolution FT-ICR MS analysis of intact full-length Ub-AA ($M^{10+}$ charge state is shown), according to the Examples. Circles represent the theoretical isotopic distribution. Calc'd and Expt'l refer to the calculated and experimental molecular weights of full length Ub-AA, respectively.

UbD77 (185.6 mg, 21.7 µM) was dissolved in a buffer containing 50 mM Hepes pH 8, 1 mM EDTA, 30% DMSO, and 250 mM allylamine to a total reaction volume of 25 mL. To this mixture was added YUH1 (25 nM). After two hours of shaking at room temperature, the reaction mixture was quenched with TFA to a pH of 1-2, exchanged into Buffer A (50 mM $NH_4Oac$ pH 4.4, 1 mM DTT, 0.5 mM EDTA) and purified by cation exchange chromatography using the same method as in the Ub purification described above. Fractions containing Ub-AA were verified by MALDI mass spectrometry, combined, concentrated, exchanged into water, and lyophilized for use in thiol-ene reactions. Final characterization was done by high resolution Fourier transform ion cyclotron resonance (FT-ICR) mass spectrometry using the methods explained below (FIG. 1).

Example 4

Synthesis of the Lithium Acyl Phosphinate (LAP) Free-Radical Photoinitiator

Lithium phenyl-2,4,6-trimethylbenzoylphosphinate (LAP) was synthesized according to the procedures described by Majima[3] and Fairbanks[4] without modifications (Scheme 1).

Scheme 1. Synthetic scheme for LAP free-radical photoinitiator.

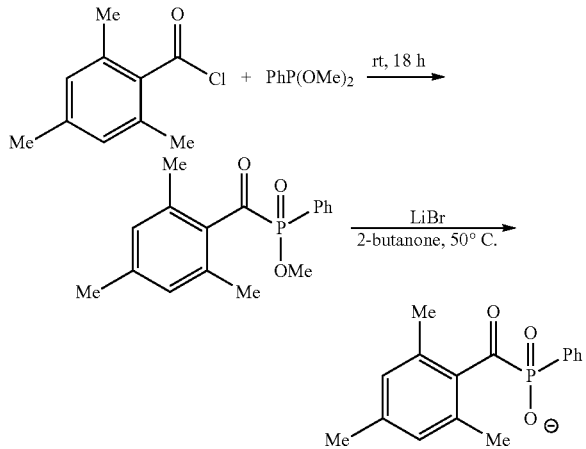

Example 5

Thiol-Ene Coupling (TEC) Reactions

Reaction Procedure.

Figure 2:
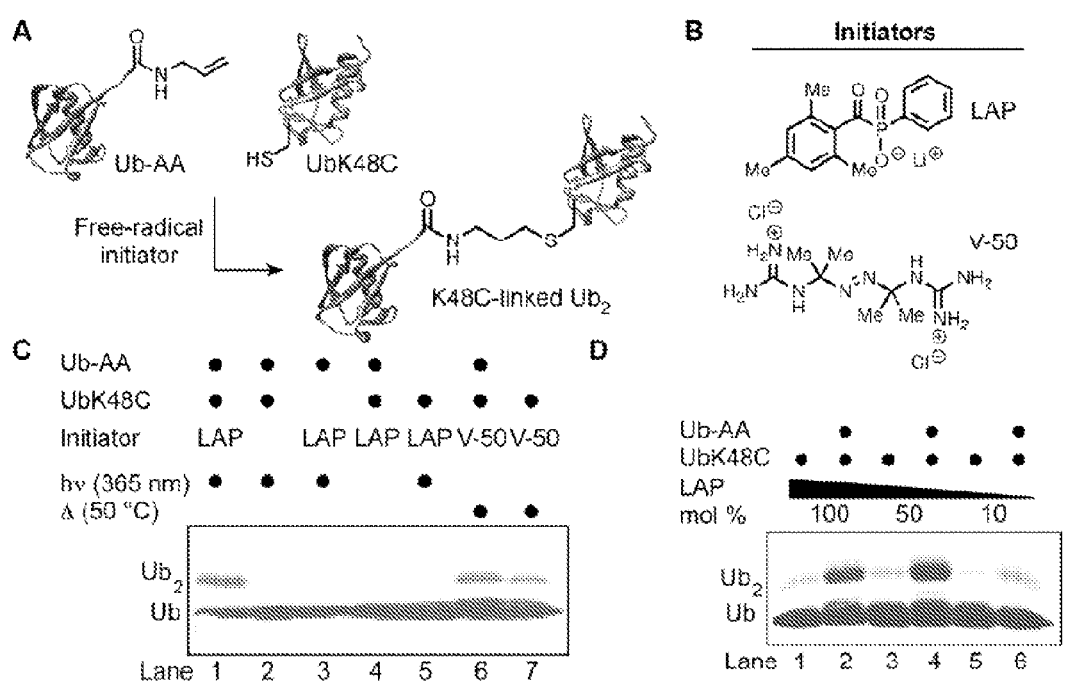
FIG. 2. Construction of K48C-linked $Ub_2$ using TEC, according to the Examples: (A) Reaction scheme for the TEC of Ub-AA and UbK48C (PDB code for Ub structure shown: 1UBQ). (B) Structures of the free-radical initiators used in this study. (C) Coomassie-stained SDS-PAGE analysis of TEC reactions carried out with different initiators. Each lane represents a reaction conducted with Ub-AA (1 mM) and UbK48C (1 mM), and free-radical initiator LAP (0.1 mM) or V-50 (100 mM) at pH 5.0. In the case of LAP, the reactions were irradiated with long wavelength light at 365 nm. Black dot indicates presence of specified reaction component. (D) SDS-PAGE analysis of TEC reactions with varying concentrations of the LAP photoinitiator.
Figure 3:
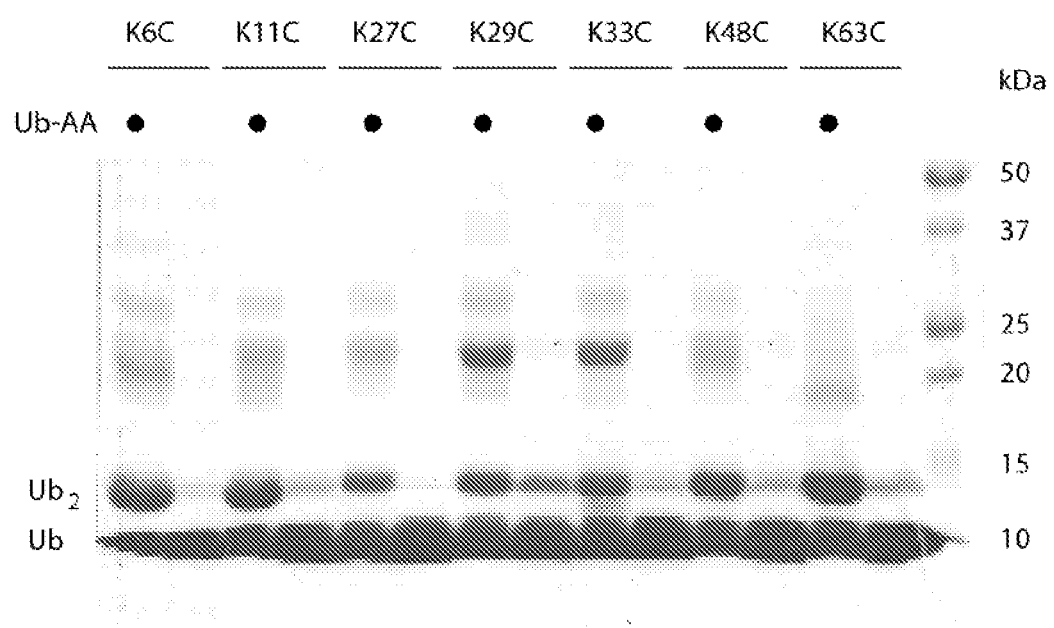
FIG. 3. Coomassie-stained SDS-PAGE analysis of TEC reactions with all seven UbKxC nmtants, according to the Examples. Dimers are observed in all reactions containing Ub-AA. The higher MW bands observed in the reactions conducted with Ub-AA are present in differing amounts depending on the UbKxC mutant.

Typical TEC reactions contained UbKxC (1 mM), Ub-AA (1 mM), LAP (0.5 mM) in 250 mM NaOAc buffer pH 5.1 (50 µL reaction volume). Samples were placed on ice and irradiated from above with 365 nM light for 30 min using an OmniCure series 1500 light source placed 15 cm away from the sample. Control reactions contained wild type Ub (1 mM)

instead of Ub-AA. TEC reactions were performed on all seven single UbKxC mutants (x=6, 11, 27, 29, 33, 48, 63) and analyzed by Coomassie-stained SDS-PAGE (FIG. 2). Control reactions omitting each reaction component show dimer dependence on all reaction components (FIG. 3). The same procedure was performed with the K6C, K48C; K11C, K48C; and K48C, K63C Ub double mutants, but in this case Ub-AA (2 mM) was used to furnish the respective branched trimers.

Purification Procedure for Ub Dimers and Trimers.

Figure 4:
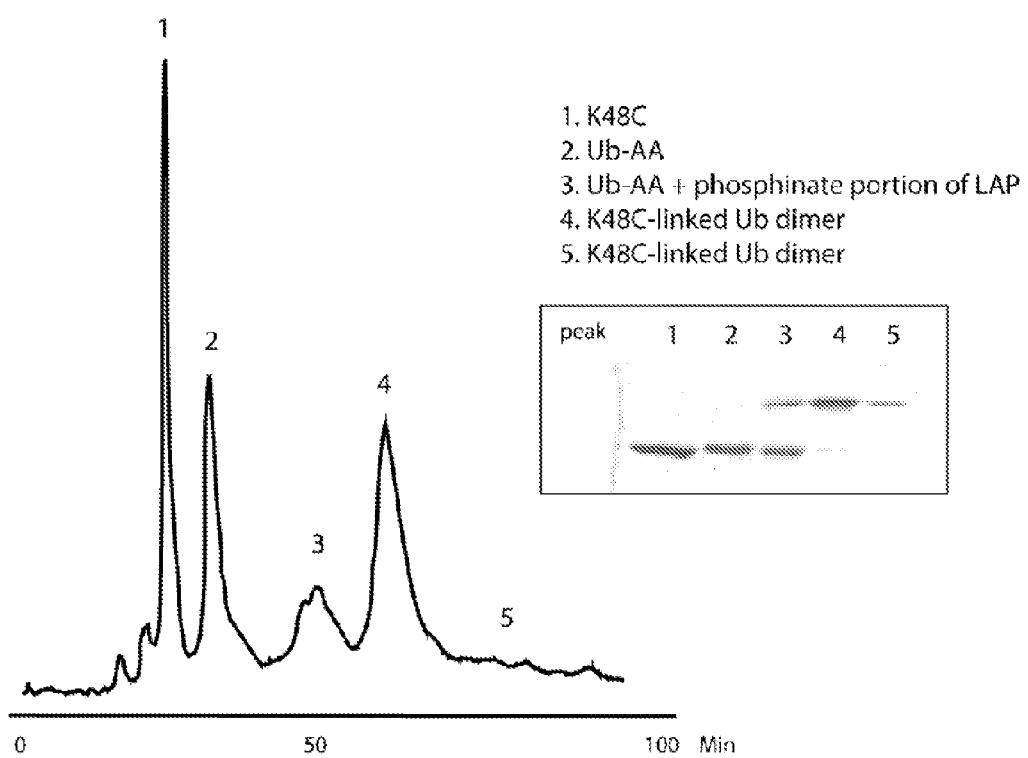
FIG. 4. Representative purification of TEC products: FPLC chromatogram for the K48C-linked Ub dimer, according to the Examples. The inset shows Coomassie-stained SDS-PAGE analysis for each peak observed in the chromatogram: peak 4 contains the purified K48C-linked Ub dimer. MS analysis of peak 3 corresponds to the mass of Ub-AA plus the phosphinate portion of the LAP photoinitiator (for more details, see below).

Multiple TEC reactions for each dimer (K6C-, K48C-, and K63C-linked) and branched trimer (K6C, K48C-; K11C, K48C-; and K48C, K63C-linked) were combined (15×50 μL) and purified by cation exchange chromatography with a gradient of 0-60% B over 35 column volumes (FIG. 4).

Example 6

MS Analysis of Intact Full-Length Ub Dimers and Trimers

General Procedure.

Crude TEC reactions for all KxC-linked Ub dimers were reduced with dithiothreitol (DTT) then desalted using Amicon 3.5 kD MW cutoff filters. Samples were dissolved in a solution of water/MeCN/acetic acid (45:45:10) and injected into a 7T linear ion trap/Fourier transform ion cyclotron resonance (LTQ/FT-ICR) hybrid mass spectrometer (Thermo Scientific Inc., Bremen, Germany) equipped with an automated chip-based nanoESI source (Triversa NanoMate, Advion BioSciences, Ithaca, N.Y.) as described previously.[5] The resolving power of the FT-ICR mass analyzer was set at 200,000. All FT-ICR spectra were processed with in-house developed Software (MadTHRASH version 1.0) using a signal to noise threshold of 3 and fit factor of 60%, and then validated manually.

Figure 5:
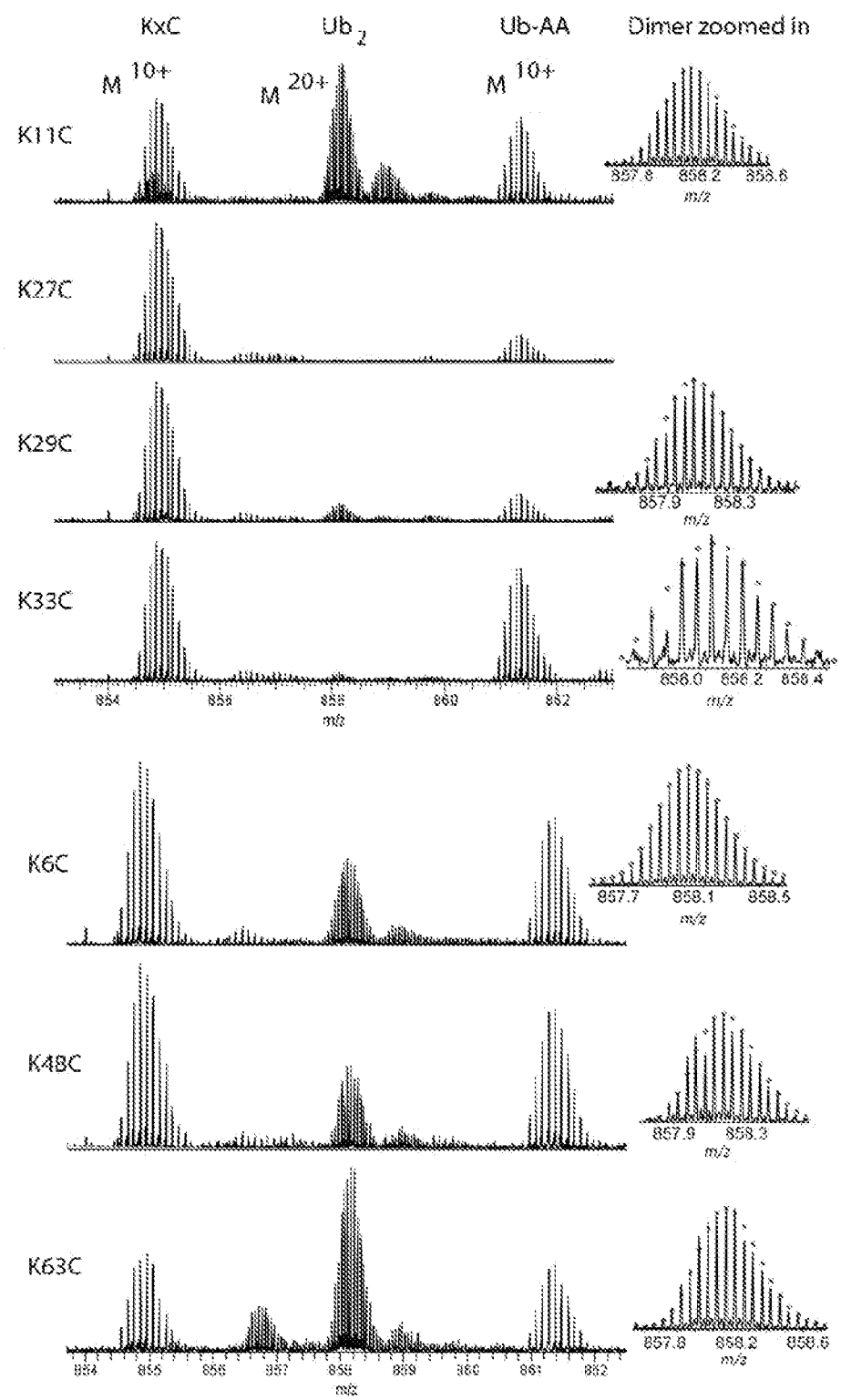
FIG. 5. High resolution FT-ICR MS analysis of crude TEC reactions using intact full-length proteins, according to the Examples. Wide view shows abundance of Ub dimers in comparison to the starting materials UbKxC and Ub-AA ($M^{10+}$ charge state for starting materials, $M^{20+}$ charge state for dimer is shown). Zoom in shows each dimer compared to the theoretical isotopic distribution (dots above peaks).
Figure 6:
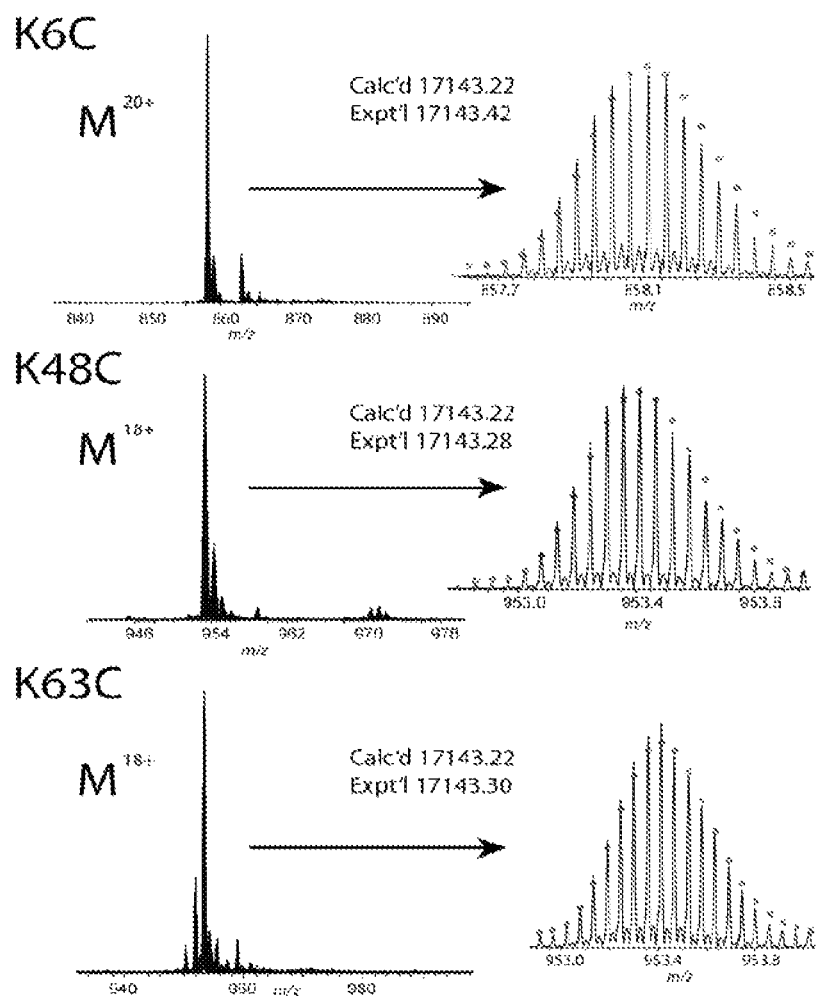
FIG. 6. High resolution FT-ICR MS analysis of each purified dimer, according to the Examples. Circles represent theoretical isotopic abundance distribution of the isotopomer peaks. Calc'd: calculated most abundant molecular weight. Expt'l: experimental most abundant molecular weight.
Figure 7:
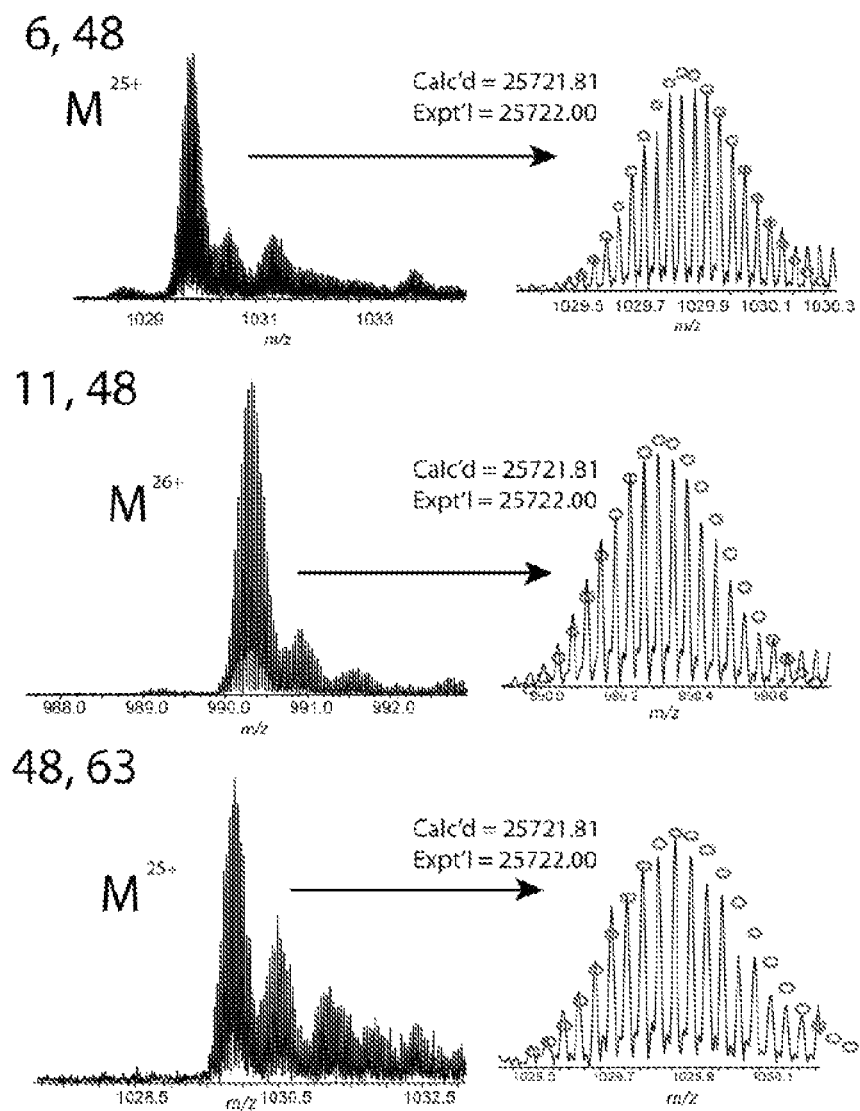
FIG. 7. FT-ICR analysis of each purified branched trimer, according to the Examples. Circles represent theoretical isotopic abundance distribution of the isotopomer peaks. Calc'd: calculated most abundant molecular weight. Expt'l: experimental most abundant molecular weight.

FIG. 5 shows the high resolution FT-ICR MS analysis of crude TEC reactions using intact full-length proteins. The wide view shows abundance of Ub dimers in comparison to the starting materials UbKxC and Ub-AA ($M^{10+}$ charge state for starting materials, $M^{2+}$ charge state for dimer is shown), while the zoom in shows each dimer compared to the theoretical isotopic distribution (dots above peaks). FIG. 6 shows the high resolution FT-ICR MS analysis of each purified dimer. Circles represent theoretical isotopic abundance distribution of the isotopomer peaks. Calc'd: calculated most abundant molecular weight. Expt'l: experimental most abundant molecular weight. Similarly, FIG. 7 shows the FT-ICR analysis of each purified branched trimer.

Example 7

Electron Capture Dissociation (ECD) Analysis of the Nε-Gly-L-homothiaLys Linkage General Procedure for ECD.

For tandem mass spectrometry (MS/MS) experiments using ECD, individual charge states of protein molecular ions were first isolated. Then, the ions were dissociated by ECD using 3% "electron energy" and a 70 ms duration with no delay. All FT-ICR spectra were processed with in-house developed Software (MadTHRASH version 1.0) using a signal to noise threshold of 3 and fit factor of 60%, and then validated manually. The resulting mass lists were further assigned based on the protein sequence of Ub with or without the modification (GlyGly-AA) at each Cys using a 10 and 20 ppm tolerance for precursor and fragment ions, respectively. All reported $M_r$ values are most abundant molecular weights.

Sample Preparation for ECD Analysis.

Purified K6C-, K48C-, and K63C-linked Ub dimers and branched Ub trimers (K6C, K48C-; K11C, K48C-; and K48C/K63C-linked) were minimally digested with trypsin (3 h digestion, 1:100 trypsin:Ub ratio) for detailed analysis of the Nε-Gly-L-homothiaLys thioether linkage. Since trypsin cleaves at position-74 of Ub, the products in this case are single Ub units missing the C-terminal GlyGly motif, but attached to GlyGly-AA at the respective cysteine residue (the product of this minimal trypsinolysis is referred to as $Ub_{1-74}$GlyGly-AA): this greatly simplifies analysis by ECD fragmentation (Scheme 2).

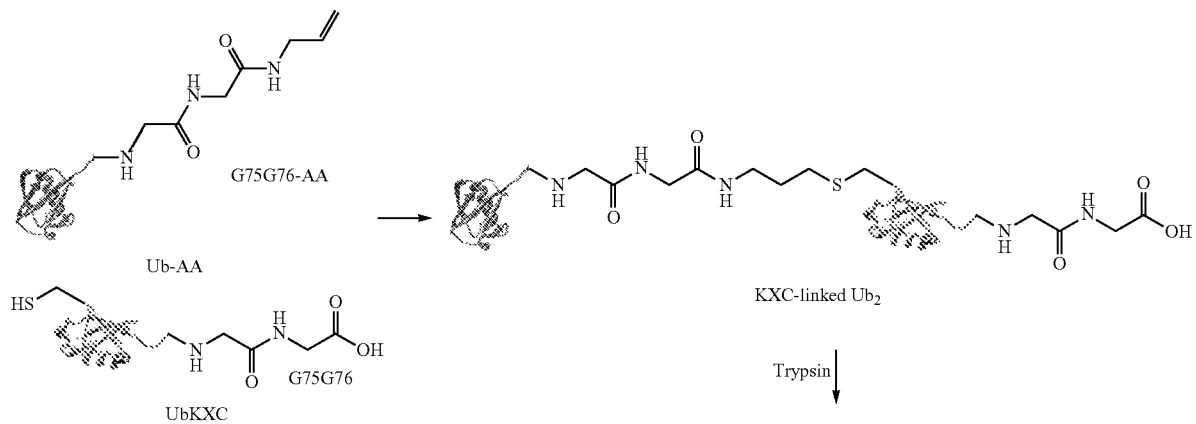

Scheme 2. ECD analysis of the N-Gly-L-homothiaLys linkage

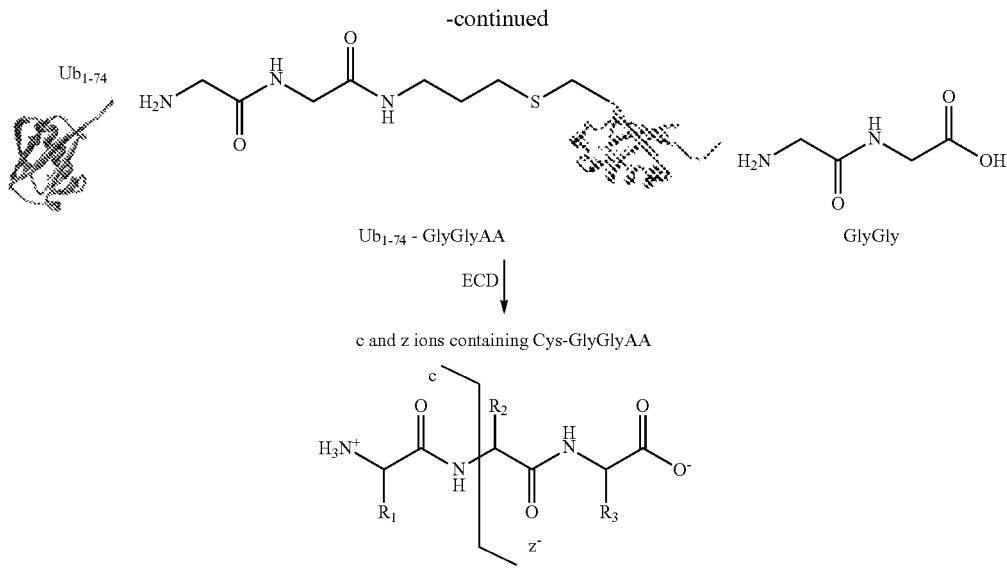

Detailed Procedure for ECD Analysis.

$Ub_{1-74}$GlyGly-AA was fragmented by ECD, and the resulting fragments were analyzed to verify the linkage at the desired cysteine. Analysis was performed using in-house data analysis software (described above). The $Ub_{1-74}$ sequence was used to predict fragment molecular weights of all possible c ions (N-terminal ions, numbered from amino acid 1) and z* ions (C-terminal ions numbered starting from 1 from the C-terminal arginine and counting in reverse of the conventional amino acid numbering scheme). Raw data were analyzed to find molecular weights of each observed fragments. Observed fragments and predicted fragments are compared to assign ion type to the observed peaks. Ion assignments were then verified and analyzed with and without inclusion of a cysteine modification in the theoretical peak predictions. When the thiol-ene modification was not taken into account in the analysis, c ions after the cysteine and z* ions before the cysteine were lacking. Upon addition of 171 amu, which represents the GlyGly-AA motif, to the molecular weight of cysteine the ion types in observed data were reassigned. In this case, the c and z* ions were both present throughout the entire sequence. This data supports the modification at the desired cysteine residue and holds true for all mutants analyzed.

Figure 8:
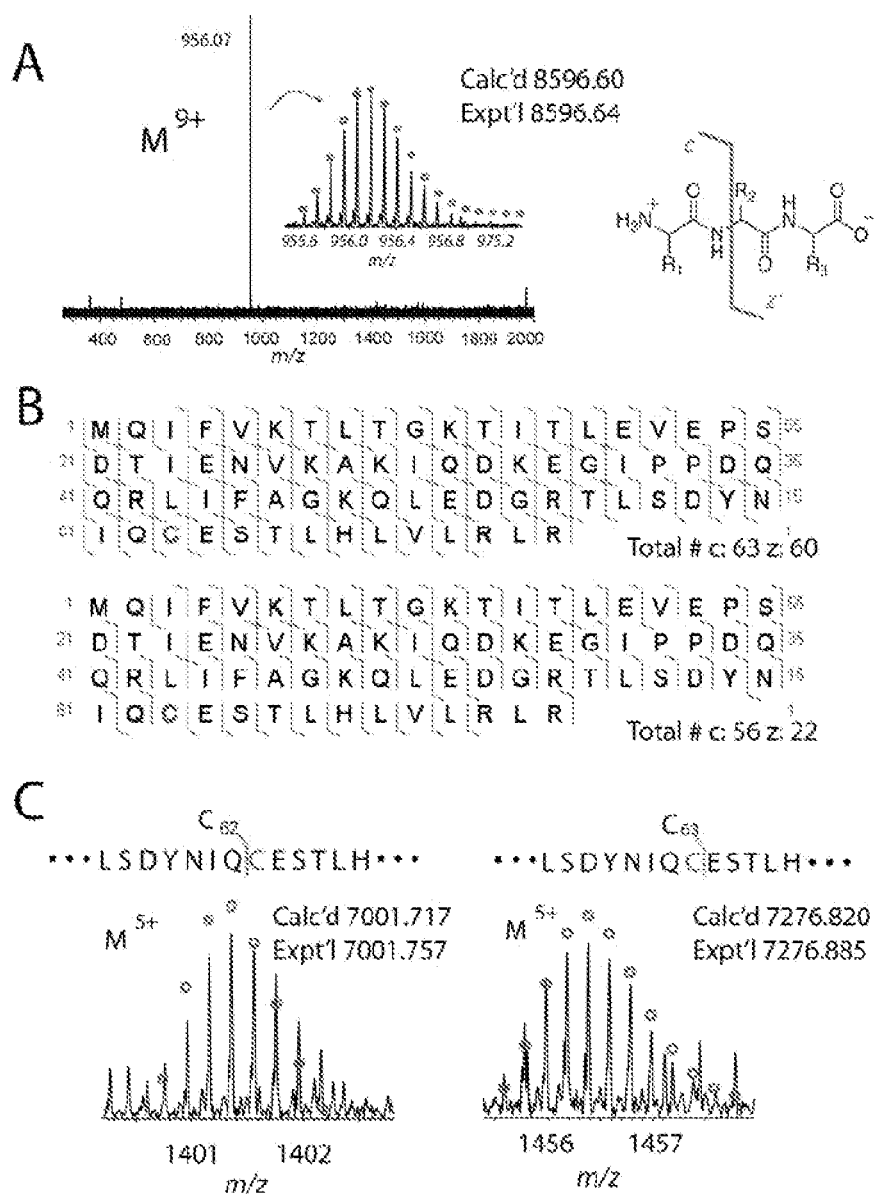
FIG. 8. ECD analysis of K63C-linked dimer, according to the Examples: (A) K63C-linked $Ub_{1-74}$ GlyGly-AA parent ion isolation ($M^{9+}$ charge state) with insert of isotopomers.

FIG. 8 shows the ECD analysis of K63C-linked dimer. FIG. 8A shows K63C-linked $Ub_{1-74}$ GlyGly-AA parent ion isolation ($M^{9+}$ charge state) with insert of isotopomers. FIG. 8B is a map of observed fragments. Data analysis for the map on top includes Nε-Gly-L-homothiaLys thioether linker modification at cysteine-63 (red) in c and z* ion predictions. Bottom map does not include thioether linker modification in theoretical analysis. FIG. 8C shows the key ECD fragment ions for mapping thioether linkage site on UbK63C. Circles represent theoretical isotopic abundance distribution of the isotopomer peaks. Calc'd: calculated most abundant molecular weight. Expt'l: experimental most abundant molecular weight.

Similarly, FIG. 9 shows the ECD analysis of K6C-linked dimer, with FIG. 9A being the K6C-linked $Ub_{1-74}$ GlyGly-AA parent ion isolation ($M^{10+}$ charge state) with insert of isotopomers. FIG. 9B is a map of observed fragments. Data analysis for the map on top includes Nε-Gly-L-homothiaLys thioether linker modification at cysteine-6 (red) in c and z* ion predictions. The bottom map does not include thioether linker modification in theoretical analysis. FIG. 9C shows the key ECD fragment ions for mapping thioether linkage site on UbK6C, where circles represent theoretical isotopic abundance distribution of the isotopomer peaks.

FIG. 10 is the ECD analysis of K48C-linked Ub dimer. FIG. 10A is K48C-linked $Ub_{1-74}$ GlyGly-AA parent ion isolation ($M^{9+}$ charge state) with insert of isotopomers, and FIG. 10B is the map of observed fragments. Data analysis for the map on top in FIG. 10B includes Nε-Gly-L-homothiaLys thioether linker modification at cysteine-48 (red) in c and z* ion predictions, while the bottom map does not include thioether linker modification in theoretical analysis.

FIG. 11 is the ECD analysis of K6C, K48C-linked branched Ub trimer, with FIG. 11A K6C, K48C $Ub_{1-74}$ GlyGlyAA$_2$ parent ion isolation ($M^{10+}$ charge state) with insert of isotopomers and FIG. 11B a map of observed fragments. Data analysis includes Nε-Gly-L-homothiaLys thioether linker modification at cysteine-6 and cysteine-48 (red) in c and z* ion predictions. FIG. 12 shows the Key ECD fragment ions for K6C, K48C-linked trimer. Circles represent theoretical isotopic abundance distribution of the isotopomer peaks. Calc'd: calculated most abundant molecular weight. Expt'l: experimental most abundant molecular weight.

FIG. 13 shows the ECD analysis of K11C, K48C-linked trimer. FIG. 13A is K11C, K48C-linked $Ub_{1-74}$ GlyGlyAA$_2$ parent ion isolation ($M^{10+}$ charge state) with insert of isotopomers and FIG. 13B is a map of observed fragments. Data analysis for the map on the top in FIG. 13B includes the Nε-Gly-L-homothiaLys thioether linker modification at cysteine-11 and cysteine-48 (red) in c and z* ion predictions. Bottom map does not include thioether linker modifications in the sequence. FIG. 14 shows the key ECD fragment ions for K11C, K48C-linked trimer. Circles represent theoretical isotopic abundance distribution of the isotopomer peaks.

FIG. 15 is the ECD analysis of K48C, K63C-linked trimer, with K48C, K63C-linked $Ub_{1-74}$ GlyGlyAA$_2$ parent ion isolation ($M^{10+}$ charge state) with insert of isotopomers (FIG. 15A) and the map of observed fragments (FIG. 15B). Data analysis in FIG. 15B for the map on top includes the Nε-Gly-L-homothiaLys thioether linker modification at cysteine-48 and cysteine-63 (red) in c and z* ion predictions, while the bottom map does not include thioether linker modifications in

Example 8

Optimization of Difficult Linkages (K27C, K29C, K33C)

TEC reactions were performed with varying amounts of Ub-AA and analyzed by high resolution FT-ICR MS. Relative amounts of product can be compared between each spectrum because the amount of UbKxC was the same in each reaction and can therefore be used as an internal standard (FIGS. 17-19).

Addition of Phosphinate Portion of LAP to Ub-AA.

Mass spectra of crude reaction mixtures shows a peak that corresponds to the mass of Ub-AA plus the phosphinate portion of the LAP photoinitiator (see FIGS. 17-19). This observation has precedent from the work of Jockusch and Turro,[6] which describes the rapid addition ($k \sim 10^7$ $M^{-1}s^{-1}$) of phosphinoyl radicals to acrylates. Based on this work we propose the process shown in Scheme 3 occurs.

Scheme 3. Proposed mechanism for the generation of Ub-AA/phosphinate adduct observed in crude reaction mixtures for the TEC reactions.

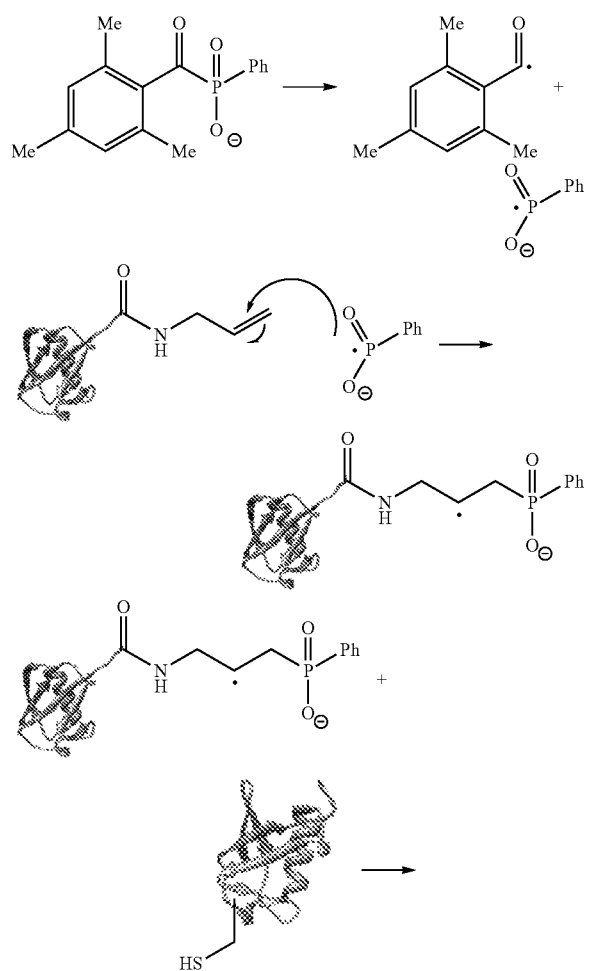

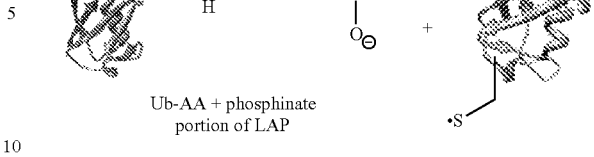

Ub-AA + phosphinate portion of LAP

Example 9

DUB-Catalyzed Hydrolysis of Ub Dimers and Trimers

General Procedure.

IsoT and A20 were purchased from Boston Biochem, while AMSH was purchased from LifeSensors. For the DUB-catalyzed hydrolysis of Ub dimers, reactions contained a particular KxC-linked Ub dimer (5 µM) and the DUB (5 µM AMSH or 500 nM A20-OTU) in the DUB reaction buffer (50 mM Tris pH 7.6, 25 mM KCl, 5 mM $MgCl_2$, 1 mM DTT) at 37° C. The DUB was added to the reaction last to initiate hydrolysis. At the time points indicated, 10 µL aliquots were taken and mixed with 3 µL of 6× Laemmli sample loading buffer. Samples were subjected to SDS-PAGE analysis and visualized using silver stain. For the DUB-catalyzed hydrolysis of Ub trimers, reactions contained Ub trimer (20 µM) and the DUB (5 µM AMSH, 500 nM A20-OTU, or 1 mM IsoT) in the DUB reaction buffer at 37° C. At the time points indicated, 10 µL aliquots were taken and mixed with 3 L of 6× Laemmli sample loading buffer. Samples were subjected to SDS-PAGE analysis and detected by western blot using anti-ubiquitin antibody (P4D1) from Cell Signaling Technologies.

In particular, K11C. K48C. K48C, K63C, and K6C, K48C-linked trimers were chosen to systematically investigate the influence of an additional Ub unit on the hydrolysis of the K48C-linkage. IsoT efficiently processed all three trimers as evidenced by Western blot analysis (FIGS. 20-22). The most striking result, however, came while studying A20-OTU-catalyzed cleavage. That is, Western blot analysis indicated A20-OTU cleaved the K48C-linkage in K11C, K48C and K48C, K63C-linked trimers, whereas the same linkage remained intact in the K6C, K48C-linked trimer. Since other nonselective DUBs such as those in the USP (Ubspecific protease) family, in particular USP7, trim K6C, K48C-linked Ub3 down to the monomer (see below and FIG. 23), the results with A20-OTU suggest the additional Ub unit appended to position-6 abrogates hydrolytic cleavage by K48-linkage selective DUBs. In the context of other linkage selective DUBs such as AMSH, the presence of a Ub appendage at position 48 does not influence cleavage of the K63C-linkage as indicated by the formation of Ub2 and Ub upon hydrolysis of the K48C, K63C-linked trimer (FIG. 21).

Our systematic examination of branched trimer topologies suggests that branch points in a polyUb chain furnish a regulatory mechanism for linkage-selective interactions. Consistent with this analysis, K6-linkages are proposed to suppress degradation of target proteins by 26S proteasomes. In principle, this could lead to the accumulation, and possibly aggregation, of the target protein, which, in turn, would set the stage for clearance by the lysosomal pathway. If the latter is either unable or slow to process the aggregated proteins bearing polyUb chains, then toxic levels may begin to accrue in the cell: this is a hallmark of many neurodegenerative diseases.

Interestingly, mixed K6-, K11-, and K48-linked polyUb chains have been observed in Tau aggregates isolated from brain tissue of individuals with Alzheimer's disease.

To provide additional support for the hydrolytic cleavage of K6C. K48C-linked branched tri-Ub with DUBs lacking linkage selectivity, we investigated the activity of USP7. USP7 is a member of the ubiquitin-specific protease (USP) family, and recently Sixnma and co-workers reported that the majority of isopeptidases in this family display little linkage selectivity.[7] The reason for specifically investigating the activity of USP7 towards the K6C, K48C-linked trimer is that Ciechanover and co-workers demonstrated the regulation of RING1B by USP7.[8] Autoubiquitylation of RING B generates a putative branched polyUb chain linked through K6, K27, and K48.[9] We surmised that if a branched chain containing K6- and K48-linkages is indeed attached to RING1B and USP7 is responsible for removing this chain, then USP7 should process K6C, K48C-linked tri-Ub. As shown in FIG. 23, dimeric and monomeric Ub products are immediately produced upon treatment of the branched chain with USP7.

Example 10

Preparation of Carboxy Terminus Modified Ubiquitin

C-Terminal Modification of Ubiquitin.

Reactions were performed at room temperature in buffer (50 mM HEPES pH 8.0, 1 mM EDTA) containing 30% DMSO, 0.7 mM Ubiquitin D77, 250 mM of indicated amine, and 250 nM YUH1. The reactions were initiated by addition of YUH1, allowed to proceed for 12 hours, and quenched with 1% TFA. Modifications were analyzed using MALDI.

(6) Jockusch, S.; Turro, N. J. *J. Am. Chem. Soc.* 1998, 120, 11773.
(7) Faesen, A. C.; Luna-Vargas, M. P.; Geurink, P. P.; Clerici, M.; Merkx, R.; van Dijk, W. J.; Hameed, D. S.; El Oualid, F.; Ovaa, H.; Sixma, T. K. *Chem. Biol.* 2011, 18, 1550.
(8) de Bie, P.; Zaaroor-Regev, D.; Ciechanover, A. *Biochem. Biophys. Res. Commun.* 2010, 400, 389.
(9) Ben-Saadon. R.; Zaaroor, D.; Ziv, T.; Ciechanover, A. *Mol. Cell* 2006, 24, 701.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art

| Amine | Structure | MW g/m | Calc'd mass Ub conjugate | Actual mass Ub conjugate |
|---|---|---|---|---|
| allylamine | H₂N-CH₂-CH=CH₂ | 57.1 | 8717.1 | |
| butylamine | H₂N-(CH₂)₃-CH₃ | 73.1 | 8733.1 | 8734.0 |
| benzylamine | H₂N-CH₂-C₆H₅ | 107.2 | 8767.2 | 8768.4 |
| (boc)ethylene diamine | H₂N-CH₂-CH₂-NHBoc | 160.2 | 8820.2 | 8820.0 |
| 2-[2-((6-Chlorohexyl)oxy)ethoxy)ethanamine | H₂N-CH₂CH₂-O-CH₂CH₂-O-(CH₂)₆-Cl | 223.7 | 8883.7 | 8884.6 |

REFERENCES (1) Ho, S. N.; Hunt, H. D.; Horton, R. M.; Pullen, J. K.; Pease, L. R. *Gene* 1989, 77, 51.
(2) Pickart, C. M.; Raasi, S. *Meth. Enzymol.* 2005, 399, 21.
(3) Majima, T.; Schnabel, W.; Weber, W. *Makromol. Chem.* 1991, 192, 2307.
(4) Fairbanks, B. D.; Schwartz, M. P.; Bowman, C. N.; Anseth, K. S. *Biomaterials* 2009, 30, 6702.
(5) (a) Ayaz-Guner, S.; Zhang, J.; Li, L.; Walker, J. W.; Ge, Y. *Biochemistry* 2009, 48, 8161. (b) Ge, Y.; Rybakova, I. N.; Xu, Q.; Moss, R. L. *Proc. Natl. Acad. Sci. USA* 2009, 106, 12658. (c) Zhang, J.; Guy, M. J.; Norman, H. S.; Chen, Y. C.; Xu, Q. G.; Dong, X. T.; Guner, H.; Wang, S. J.; Kohmoto, T.; Young, K. H.; Moss. R. L.; Ge, Y. *J. Proteome Res.* 2011, 10, 4054.

will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An oligomer comprising two or more monomers wherein each monomer is independently selected from a ubiquitin polypeptide or a ubiquitin-like polypeptide, the monomers are covalently linked to each other via a thioether group or groups; each thioether group comprises a cysteine residue of one of the monomers and the carboxy terminus of another monomer; each cysteine residue in the thioether group replaces a lysine residue in the native sequence of the monomer; and each thioether group is of the formula

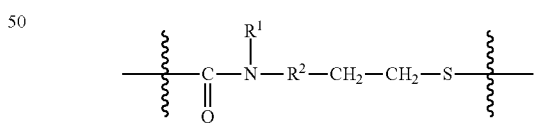

where $R^1$ is H or a $C_1$-$C_4$ alkyl group;

$R^2$ is a substituted or unsubstituted alkylene, alkylene oxide, arylene, or aralkylene group;

C=O is a carbonyl group of the carboxy terminus; and

S is a sulfur of the cysteine residue.

2. The oligomer of claim 1, wherein each monomer is a mutant in which each cysteine residue in the thioether group replaces a lysine residue in the native sequence of the monomer.

3. The oligomer of claim 1 comprising 2, 3, 4, 5, 6, 7, 8, 9 or 10 monomers.

4. The oligomer of claim 1 wherein the oligomer is linear.

5. The oligomer of claim 1 wherein the oligomer is branched.

6. The oligomer of claim 5 wherein at least one monomer is covalently linked to at least 2 other monomers via thioether groups to the peptide backbone of the at least one monomer.

7. The oligomer of claim 1 wherein the thioether groups of at least two monomers comprise cysteines at different positions within the monomer.

8. The oligomer of claim 7 wherein at least one monomer comprises a thioether group at K6C and a thioether group at K48C, or at K11C and K48C, or at K48C and K63C.

9. The oligomer of claim 1 wherein each monomer is independently selected from a polypeptide that
 a. has at least 95% sequence identity to a sequence selected from the group consisting of SEQ ID NOS:1, 2, 3, 4, and 5;
 b. comprises a sequence that has at least 95% sequence identity to a sequence selected from the group consisting of SEQ ID NOS:1, 2, 3, 4, and 5; or
 c. is a fragment of a polypeptide having at least 95% sequence identity to a sequence selected from the group consisting of SEQ ID NOS:1, 2, 3, 4, and 5;
 wherein the ubiquitin or ubiquitin-like polypeptide is a substrate for a deubiquinating enzyme or for proteins containing ubiquitin-binding domains when covalently attached via its carboxy terminus to another protein.

10. A conjugate comprising an oligomer of claim 1 covalently attached to a non-ubiquitin or non-ubiquitin-like polypeptide.

11. The conjugate of claim 10 wherein the oligomer is attached to the non-ubiquitin or non-ubiquitin-like polypeptide through the carboxy terminus of one of the monomers in the oligomer.

12. The oligomer of claim 6 comprising 3, 4, 5, 6, 7, 8, 9 or 10 monomers.

13. The oligomer of claim 6 wherein the thioether groups of at least two monomers comprise cysteines at different positions within the monomer.

14. The oligomer of claim 13 wherein at least one monomer comprises a thioether group at K6C and a thioether group at K48C, or at K11C and K48C, or at K48C and K63C.

15. The oligomer of claim 6 wherein each monomer is independently selected from a polypeptide that
 a. has at least 95% sequence identity to a sequence selected from the group consisting of SEQ ID NOS:1, 2, 3, 4, and 5;
 b. comprises a sequence that has at least 95% sequence identity to a sequence selected from the group consisting of SEQ ID NOS:1, 2, 3, 4, and 5; or
 c. is a fragment of a polypeptide having at least 95% sequence identity to a sequence selected from the group consisting of SEQ ID NOS:1, 2, 3, 4, and 5;
 wherein the ubiquitin or ubiquitin-like polypeptide is a substrate for a deubiquinating enzyme or for proteins containing ubiquitin-binding domains when covalently attached via its carboxy terminus to another protein.

16. A conjugate comprising an oligomer of claim 6 covalently attached to a non-ubiquitin or non-ubiquitin-like polypeptide.

17. The conjugate of claim 16 wherein the oligomer is attached to the non-ubiquitin or non-ubiquitin-like polypeptide through the carboxy terminus of one of the monomers in the oligomer.

18. A method of making an oligomer of claim 1 comprising coupling a first monomer to a second monomer under free radical conditions such that the first and second monomers are linked by a thioether group, wherein the first monomer is selected from a ubiquitin or ubiquitin-like polypeptide comprising a carboxy terminal alkenyl group of the formula

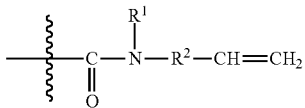

where
 $R^1$ is H or a $C_1$-$C_4$ alkyl group; and
 $R^2$ is a substituted or unsubstituted alkylene, alkylene oxide, arylene, or aralkylene group; and
 C=O is a carbonyl group of the carboxy terminus;
and the second monomer is selected from a ubiquitin or ubiquitin-like polypeptide comprising one or more cysteine residues; and each cysteine residue in the thioether group replaces a lysine residue in the native sequence of the monomer.

19. The method of claim 18 wherein the ubiquitin or ubiquitin polypeptide
 a. has at least 95% sequence identity to a sequence selected from the group consisting of SEQ ID NOS:1, 2, 3, 4, and 5;
 b. comprises a sequence that has at least 95% sequence identity to a sequence selected from the group consisting of SEQ ID NOS:1, 2, 3, 4, and 5; or
 c. is a fragment of a polypeptide having at least 95% sequence identity to a sequence selected from the group consisting of SEQ ID NOS:1, 2, 3, 4, and 5,
 wherein the ubiquitin or ubiquitin-like polypeptide is a substrate for a deubiquinating enzyme when covalently attached via its carboxy terminus to another protein.

20. The method of claim 18 wherein the coupling is carried out in the presence of a free radical initiator.

21. The method of claim 20 wherein the coupling is carried out under sufficient ultraviolet light to generate free radicals.

22. The method of claim 20 wherein the free radical initiator is selected from a lithium acyl phosphinate or a water soluble 2,2-dimethoxy-2-phenylacetophenone.

23. The method of claim 18 wherein the second monomer comprises a carboxy terminal alkenyl group of the formula

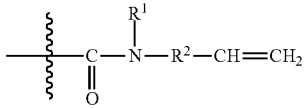

where
 $R^1$ is H or a $C_1$-$C_4$ alkyl group; and
 $R^2$ is a substituted or unsubstituted alkylene, alkylene oxide, arylene, or aralkylene group; and
 C=O is a carbonyl group of the carboxy terminus;
and is coupled to a third monomer under free radical conditions to form a thioether group and the third monomer is selected from a ubiquitin or ubiquitin-like polypeptide comprising one or more cysteine residues.

24. The method of claim 18 wherein the second monomer comprises two cysteine residues and the second monomer is coupled to a third monomer under free radical conditions to form a thioether group, wherein the third monomer comprises a carboxy terminal alkenyl group of the formula

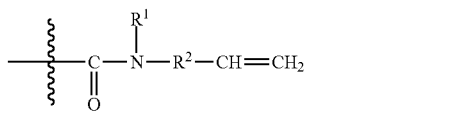
where
- $R^1$ is H or a $C_1$-$C_4$ alkyl group; and
- $R^2$ is a substituted or unsubstituted alkylene, alkylene oxide, arylene, or aralkylene group; and
- C=O is a carbonyl group of the carboxy terminus.
\* \* \* \* \*